US009709509B1

(12) United States Patent
Yang

(10) Patent No.: US 9,709,509 B1
(45) Date of Patent: *Jul. 18, 2017

(54) SYSTEM CONFIGURED FOR INTEGRATED COMMUNICATION, MEMS, PROCESSOR, AND APPLICATIONS USING A FOUNDRY COMPATIBLE SEMICONDUCTOR PROCESS

(75) Inventor: Xiao "Charles" Yang, Cupertino, CA (US)

(73) Assignee: mCube Inc., San Jose, CA (US)

( * ) Notice: Subject to any disclaimer, the term of this patent is extended or adjusted under 35 U.S.C. 154(b) by 614 days.

This patent is subject to a terminal disclaimer.

(21) Appl. No.: 12/944,712

(22) Filed: Nov. 11, 2010

Related U.S. Application Data

(60) Provisional application No. 61/260,846, filed on Nov. 13, 2009.

(51) Int. Cl.
*G01L 1/00* (2006.01)
*G01L 7/00* (2006.01)
*G01L 9/00* (2006.01)
*G01L 11/00* (2006.01)
*G01L 19/00* (2006.01)
*G01N 7/00* (2006.01)
*G01N 21/95* (2006.01)

(52) U.S. Cl.
CPC . *G01N 21/9501* (2013.01); *G01N 2291/0258* (2013.01)

(58) Field of Classification Search
CPC .................. G01N 2291/0258; G01N 21/9501
USPC ........................................... 702/127, 138, 35
See application file for complete search history.

(56) References Cited

U.S. PATENT DOCUMENTS

| | | |
|---|---|---|
| 3,614,677 A | 10/1971 | Wilfinger |
| 4,954,698 A | 9/1990 | Yasunaga et al. |
| 5,140,745 A | 8/1992 | McKenzie |
| 5,157,841 A | 10/1992 | Dinsmore |
| 5,173,597 A | 12/1992 | Anglin |
| 5,493,769 A | 2/1996 | Sakai et al. |
| 5,610,414 A | 3/1997 | Yoneda et al. |
| 5,668,033 A | 9/1997 | Ohara |
| 5,729,074 A | 3/1998 | Shiomi et al. |
| 6,046,409 A | 4/2000 | Ishii et al. |
| 6,076,731 A | 6/2000 | Terrell |

(Continued)

OTHER PUBLICATIONS

International Search Report and Written Opinion of PCT Application No. PCT/US10/054567, mailed on Jan. 6, 2011, 7 pages total.

(Continued)

*Primary Examiner* — Michael Nghiem
(74) *Attorney, Agent, or Firm* — Kilpatrick Townsend & Stockton LLP

(57) ABSTRACT

A sensor processor system is provided on a platform including a semiconductor substrate. The system has multiple integrated subsystems including a micro controller unit provided on one or more first regions of the semiconductor substrate. The subsystems also include an array of programmable memory provided on one or more second regions of the semiconductor substrate, among other elements. The subsystems also include one or more MEMS devices operably coupled to the micro controller unit. In one or more embodiments, an application processor is coupled to the semiconductor substrate and, optionally, a baseband processor is coupled to the semiconductor substrate.

12 Claims, 19 Drawing Sheets

(56) References Cited

U.S. PATENT DOCUMENTS

| | | |
|---|---|---|
| 6,115,261 A | 9/2000 | Platt et al. |
| 6,188,322 B1 | 2/2001 | Yao |
| 6,263,736 B1 | 7/2001 | Thunder et al. |
| 6,278,178 B1 | 8/2001 | Kwon et al. |
| 6,480,699 B1 | 11/2002 | Lovoi |
| 6,483,172 B1 | 11/2002 | Cote |
| 6,485,273 B1 | 11/2002 | Goodwin-Johansson |
| 6,534,726 B1 | 3/2003 | Okada et al. |
| 6,656,604 B2 | 12/2003 | Hasewaga |
| 6,753,664 B2 | 6/2004 | Neufeld et al. |
| 6,855,572 B2 | 2/2005 | Jeun et al. |
| 6,912,336 B2 | 6/2005 | Ishii |
| 6,933,165 B2 | 8/2005 | Musolf et al. |
| 7,019,434 B2 | 3/2006 | Helmbrecht |
| 7,095,226 B2 | 8/2006 | Wan et al. |
| 7,145,555 B2 | 12/2006 | Taylor et al. |
| 7,183,630 B1 | 2/2007 | Fogelson et al. |
| 7,195,945 B1 | 3/2007 | Edelstein et al. |
| 7,239,000 B2 | 7/2007 | Witcraft |
| 7,253,079 B2 | 8/2007 | Hanson et al. |
| 7,258,009 B2 | 8/2007 | Imai |
| 7,358,724 B2 | 4/2008 | Taylor et al. |
| 7,370,530 B2 | 5/2008 | DCamp et al. |
| 7,391,091 B2 | 6/2008 | Tondra |
| 7,402,449 B2 | 7/2008 | Fukuda et al. |
| 7,430,674 B2 | 9/2008 | Van Mueller et al. |
| 7,454,705 B2 | 11/2008 | Cadez et al. |
| 7,456,042 B2 | 11/2008 | Stark |
| 7,493,496 B2 | 2/2009 | Smith et al. |
| 7,498,715 B2 | 3/2009 | Yang |
| 7,511,379 B1 | 3/2009 | Flint |
| 7,514,760 B1 | 4/2009 | Quevy |
| 7,521,783 B2 | 4/2009 | Tsai et al. |
| 7,536,909 B2 | 5/2009 | Zhao et al. |
| 7,599,277 B1 | 10/2009 | Kato et al. |
| 7,612,443 B1 | 11/2009 | Bernstein et al. |
| 7,671,478 B2 | 3/2010 | Wathanawasam et al. |
| 7,676,340 B2 | 3/2010 | Yasui |
| 7,690,255 B2 | 4/2010 | Gogoi et al. |
| 7,708,189 B2 | 5/2010 | Cipriano |
| 7,713,785 B1 | 5/2010 | Flint |
| 7,779,689 B2 | 8/2010 | Li et al. |
| 7,814,791 B2 | 10/2010 | Andersson et al. |
| 7,814,792 B2 | 10/2010 | Tateyama et al. |
| 7,814,793 B2 | 10/2010 | Sato |
| 7,861,422 B2 | 1/2011 | MacDonald |
| 7,891,103 B2 | 2/2011 | Mayor |
| 8,011,577 B2 | 9/2011 | Mullen et al. |
| 8,016,191 B2 | 9/2011 | Bonalle et al. |
| 8,037,758 B2 | 10/2011 | Sato |
| 8,056,412 B2 | 11/2011 | Rutkiewicz et al. |
| 8,061,049 B2 | 11/2011 | Mayor |
| 8,070,055 B2 | 12/2011 | Block et al. |
| 8,087,296 B2 | 1/2012 | Ueda et al. |
| 8,140,358 B1* | 3/2012 | Ling et al. ............ 705/4 |
| 8,148,808 B2 | 4/2012 | Braden et al. |
| 8,165,323 B2 | 4/2012 | Zhou |
| 8,181,874 B1 | 5/2012 | Wan et al. |
| 8,227,285 B1 | 7/2012 | Yang |
| 8,236,577 B1 | 8/2012 | Hsu |
| 8,245,923 B1 | 8/2012 | Merrill et al. |
| 8,250,921 B2 | 8/2012 | Nasiri et al. |
| 8,259,311 B2 | 9/2012 | Petschko |
| 8,324,047 B1 | 12/2012 | Yang |
| 8,342,021 B2 | 1/2013 | Oshio |
| 8,367,522 B1 | 2/2013 | Yang |
| 8,395,252 B1 | 3/2013 | Yang |
| 8,395,381 B2 | 3/2013 | Lo |
| 8,402,666 B1 | 3/2013 | Hsu et al. |
| 8,407,905 B1 | 4/2013 | Hsu et al. |
| 8,421,082 B1 | 4/2013 | Yang |
| 8,476,084 B1 | 7/2013 | Yang et al. |
| 8,476,129 B1 | 7/2013 | Jensen et al. |
| 8,477,473 B1* | 7/2013 | Koury, Jr. ............ G01P 15/125 361/280 |
| 8,486,723 B1* | 7/2013 | Wan et al. .................. 438/3 |
| 8,553,389 B1* | 10/2013 | Koury et al. .............. 361/287 |
| 8,710,597 B1* | 4/2014 | Koury, Jr. ............ B81C 1/00134 257/252 |
| 8,742,520 B2* | 6/2014 | Wan et al. .................. 257/421 |
| 8,823,007 B2* | 9/2014 | Yang ............ B81C 1/00246 257/204 |
| 8,936,959 B1* | 1/2015 | Yang ............ B81C 1/00238 438/48 |
| 2001/0053565 A1 | 12/2001 | Khoury |
| 2002/0072163 A1 | 6/2002 | Wong et al. |
| 2002/0134837 A1 | 9/2002 | Kishon |
| 2003/0058069 A1 | 3/2003 | Schwartz et al. |
| 2003/0095115 A1 | 5/2003 | Brian et al. |
| 2003/0133489 A1 | 7/2003 | Hirota et al. |
| 2003/0184189 A1 | 10/2003 | Sinclair |
| 2004/0002808 A1 | 1/2004 | Hashimoto et al. |
| 2004/0016995 A1 | 1/2004 | Kuo et al. |
| 2004/0017644 A1 | 1/2004 | Goodwin-Johansson |
| 2004/0056742 A1 | 3/2004 | Dabbaj |
| 2004/0063325 A1* | 4/2004 | Urano et al. .................. 438/692 |
| 2004/0104268 A1 | 6/2004 | Bailey |
| 2004/0113246 A1 | 6/2004 | Boon |
| 2004/0119836 A1 | 6/2004 | Kitaguchi et al. |
| 2004/0140962 A1 | 7/2004 | Wang et al. |
| 2004/0177045 A1 | 9/2004 | Brown |
| 2004/0207035 A1 | 10/2004 | Witcraft et al. |
| 2004/0227201 A1 | 11/2004 | Borwick et al. |
| 2005/0074147 A1 | 4/2005 | Smith et al. |
| 2005/0174338 A1* | 8/2005 | Ing et al. ............ 345/177 |
| 2005/0199791 A1 | 9/2005 | Sengoku et al. |
| 2005/0247787 A1 | 11/2005 | Von Mueller et al. |
| 2005/0252293 A1 | 11/2005 | Won et al. |
| 2006/0049826 A1 | 3/2006 | Daneman et al. |
| 2006/0081954 A1 | 4/2006 | Tondra et al. |
| 2006/0141786 A1 | 6/2006 | Boezen et al. |
| 2006/0168832 A1 | 8/2006 | Yasui et al. |
| 2006/0192465 A1 | 8/2006 | Kornbluh et al. |
| 2006/0208326 A1 | 9/2006 | Nasiri et al. |
| 2006/0211044 A1* | 9/2006 | Green ............ 435/7.1 |
| 2006/0238621 A1 | 10/2006 | Okubo et al. |
| 2006/0243049 A1 | 11/2006 | Ohta et al. |
| 2006/0274399 A1 | 12/2006 | Yang |
| 2007/0046239 A1 | 3/2007 | Hashizume |
| 2007/0132733 A1* | 6/2007 | Ram ............ 345/163 |
| 2007/0152976 A1 | 7/2007 | Townsend et al. |
| 2007/0181962 A1 | 8/2007 | Partridge et al. |
| 2007/0200564 A1 | 8/2007 | Motz et al. |
| 2007/0281379 A1 | 12/2007 | Stark et al. |
| 2008/0014682 A1 | 1/2008 | Yang et al. |
| 2008/0066547 A1 | 3/2008 | Tanaka et al. |
| 2008/0110259 A1 | 5/2008 | Takeno |
| 2008/0119000 A1 | 5/2008 | Yeh et al. |
| 2008/0123242 A1 | 5/2008 | Zhou |
| 2008/0210007 A1 | 9/2008 | Yamaji et al. |
| 2008/0211043 A1 | 9/2008 | Chen |
| 2008/0211113 A1 | 9/2008 | Chua et al. |
| 2008/0211450 A1 | 9/2008 | Yamada et al. |
| 2008/0277747 A1* | 11/2008 | Ahmad ............ 257/415 |
| 2008/0283991 A1 | 11/2008 | Reinert |
| 2009/0007661 A1 | 1/2009 | Nasiri et al. |
| 2009/0015251 A1 | 1/2009 | Azumi et al. |
| 2009/0049911 A1 | 2/2009 | Fukuda et al. |
| 2009/0108440 A1 | 4/2009 | Meyer et al. |
| 2009/0115412 A1 | 5/2009 | Fuse |
| 2009/0139330 A1* | 6/2009 | Pavelescu et al. ......... 73/514.32 |
| 2009/0139331 A1* | 6/2009 | Axelrod et al. ............ 73/514.32 |
| 2009/0153500 A1 | 6/2009 | Cho et al. |
| 2009/0262074 A1 | 10/2009 | Nasiri et al. |
| 2009/0267906 A1 | 10/2009 | Schroderus |
| 2009/0307557 A1* | 12/2009 | Rao et al. ............ 714/749 |
| 2009/0321510 A1 | 12/2009 | Day et al. |
| 2010/0014146 A1* | 1/2010 | Lan ............ B81C 1/0023 359/290 |
| 2010/0044121 A1 | 2/2010 | Simon et al. |
| 2010/0045282 A1 | 2/2010 | Shibasaki et al. |
| 2010/0071467 A1 | 3/2010 | Nasiri et al. |
| 2010/0075481 A1 | 3/2010 | Yang |
| 2010/0083756 A1 | 4/2010 | Merz et al. |

(56) References Cited

U.S. PATENT DOCUMENTS

| | | |
|---|---|---|
| 2010/0095769 A1 | 4/2010 | Matsumoto et al. |
| 2010/0109102 A1 | 5/2010 | Chen et al. |
| 2010/0170341 A1* | 7/2010 | Dwyer et al. .............. 73/514.31 |
| 2010/0171570 A1 | 7/2010 | Chandrahalim |
| 2010/0208118 A1 | 8/2010 | Ueyama |
| 2010/0231211 A1* | 9/2010 | Edelstein et al. ............. 324/244 |
| 2010/0236327 A1 | 9/2010 | Mao |
| 2010/0248662 A1 | 9/2010 | Sheynblat et al. |
| 2010/0260388 A1 | 10/2010 | Garrett et al. |
| 2010/0302199 A1 | 12/2010 | Taylor et al. |
| 2010/0306117 A1 | 12/2010 | Terayoko |
| 2010/0307016 A1 | 12/2010 | Mayor et al. |
| 2010/0312519 A1 | 12/2010 | Huang et al. |
| 2011/0131825 A1 | 6/2011 | Mayor et al. |
| 2011/0146401 A1 | 6/2011 | Inaguma et al. |
| 2011/0154905 A1* | 6/2011 | Hsu ....................... G01L 9/0073 73/724 |
| 2011/0172918 A1 | 7/2011 | Tome |
| 2011/0183456 A1 | 7/2011 | Hsieh et al. |
| 2011/0198395 A1 | 8/2011 | Chen |
| 2011/0265574 A1* | 11/2011 | Yang .............................. 73/658 |
| 2011/0266340 A9 | 11/2011 | Block et al. |
| 2011/0312349 A1 | 12/2011 | Forutanpour et al. |
| 2012/0007597 A1 | 1/2012 | Seeger et al. |
| 2012/0007598 A1 | 1/2012 | Lo et al. |
| 2012/0215475 A1 | 8/2012 | Rutledge et al. |

OTHER PUBLICATIONS

U.S. Appl. No. 12/913,440, Final Office Action mailed Oct. 10, 2013, 16 pages.

U.S. Appl. No. 12/913,440, Final Office Action mailed Feb. 10, 2014, 16 pages.

U.S. Appl. No. 12/913,440, Notice of Allowance mailed Apr. 25, 2014, 7 pages.

U.S. Appl. No. 12/983,309 Notice of Allowance mailed Aug. 13, 2013, 11 pages.

U.S. Appl. No. 13/924,457 Notice of Allowance mailed Jan. 24, 2014, 11 pages.

U.S. Appl. No. 13/924,457 Notice of Allowance mailed Sep. 18, 2013, 8 pages.

U.S. Appl. No. 13/035,969 Non-Final Office Action mailed Oct. 25, 2013, 12 pages.

U.S. Appl. No. 13/035,969 Notice of Allowance mailed Jun. 16, 2014, 10 pages.

U.S. Appl. No. 12/787,368 Non-Final Office Action mailed Sep. 19, 2013, 19 pages.

U.S. Appl. No. 12/787,368 Notice of Allowance mailed Jan. 14, 2014, 9 pages.

U.S. Appl. No. 13/922,983 Notice of Allowance mailed Oct. 7, 2013, 11 pages.

U.S. Appl. No. 13/922,983 Notice of Allowance mailed Feb. 10, 2014, 6 pages.

U.S. Appl. No. 12/787,200 Notice of Allowance mailed Sep. 26, 2013, 11 pages.

U.S. Appl. No. 13/117,053 Non-Final Office Action mailed Sep. 18, 2013, 13 pages.

U.S. Appl. No. 13/117,053 Final Office Action mailed Apr. 24, 2014, 17 pages.

U.S. Appl. No. 13/164,311 Notice of Allowance mailed Sep. 17, 2013, 8 pages.

U.S. Appl. No. 13/163,672 Non-Final Office Action mailed Sep. 5, 2013, 8 pages.

U.S. Appl. No. 13/163,672 Final Office Action mailed Feb. 26, 2014, 9 pages.

U.S. Appl. No. 13/163,672 Notice of Allowance mailed Jun. 23, 2014, 7 pages.

U.S. Appl. No. 12/940,025 Notice of Allowance mailed Oct. 17, 2013, 10 pages.

U.S. Appl. No. 13/069,355 Final Office Action mailed Nov. 1, 2013, 15 pages.

U.S. Appl. No. 13/069,355 Notice of Allowance mailed Aug. 29, 2014, 12 pages.

* cited by examiner

SYSTEM CONFIGURED FOR INTEGRATED COMMUNICATION, MEMS, PROCESSOR, AND APPLICATIONS USING A FOUNDRY COMPATIBLE SEMICONDUCTOR PROCESS

CROSS-REFERENCES TO RELATED APPLICATIONS

The present application claims priority to and incorporates by reference, for all purposes, the following patent application: U.S. Pat. App. No. 61/260,846, filed Nov. 13, 2009. The present invention also incorporates by reference, for all purposes, the following patent applications: U.S. patent application Ser. No. 12/859,631, filed Aug. 19, 2010, now U.S. Pat. No. 8,486,723, U.S. Pat. App. No. 61/356,467, filed Jun. 18, 2010, U.S. patent application Ser. No. 12/859,672, now U.S. Pat. No. 8,477,473, filed Aug. 19, 2010, U.S. patent application Ser. No. 12/859,647, filed Aug. 19, 2010, now U.S. Pat. No. 8,553,389, and U.S. patent application Ser. No. 12/913,440, filed Oct. 27, 2010.

BACKGROUND OF THE INVENTION

The present invention relates generally to integrated devices. More particularly, the present invention provides a system and method for integrating at least two different micro electro mechanical systems (MEMS) devices with one or more complementary metal oxide semiconductor (CMOS) devices. Merely by way of example, the MEMS devices can include an accelerometer, a gyroscope, a magnetic sensor, a pressure sensor, a microphone, a humidity sensor, a temperature sensor, a chemical sensor, a biosensor, an inertial sensor, and others. But it will be recognized that the invention has a much broader range of applicability.

Research and development in integrated microelectronics have continued to produce astounding progress in CMOS and MEMS. CMOS technology has become the predominant fabrication technology for integrated circuits (IC). MEMS, however, continues to rely upon conventional process technologies. In layman's terms, microelectronic ICs are the "brains" of an integrated device which provides decision-making capabilities, whereas MEMS are the "eyes" and "arms" that provide the ability to sense and control the environment. Some examples of the widespread application of these technologies are the switches in radio frequency (RF) antenna systems, such as those in the iPhone™ device by Apple, Inc. of Cupertino, Calif., and the Blackberry™ phone by Research In Motion Limited of Waterloo, Ontario, Canada, and accelerometers in sensor-equipped game devices, such as those in the Wii™ controller manufactured by Nintendo Company Limited of Japan. Though they are not always easily identifiable, these technologies are becoming ever more prevalent in society every day.

Beyond consumer electronics, use of IC and MEMS has limitless applications through modular measurement devices such as accelerometers, gyroscopes, actuators, and sensors. In conventional vehicles, accelerometers and gyroscopes are used to deploy airbags and trigger dynamic stability control functions, respectively. MEMS gyroscopes can also be used for image stabilization systems in video and still cameras, and automatic steering systems in airplanes and torpedoes. Biological MEMS (Bio-MEMS) implement biosensors and chemical sensors for Lab-On-Chip applications, which integrate one or more laboratory functions on a single millimeter-sized chip only. Other applications include Internet and telephone networks, security and financial applications, and health care and medical systems. As described previously, ICs and MEMS can be used to practically engage in various type of environmental interaction.

Although highly successful, ICs and in particular MEMS still have limitations. Similar to IC development, MEMS development, which focuses on increasing performance, reducing size, and decreasing cost, continues to be challenging. Additionally, applications of MEMS often require increasingly complex microsystems that desire greater computational power. Unfortunately, such applications generally do not exist. These and other limitations of conventional MEMS and ICs may be further described throughout the present specification and more particularly below.

From the above, it is seen that techniques for improving operation of integrated circuit devices and MEMS are highly desired.

BRIEF SUMMARY OF THE INVENTION

According to the present invention, techniques related generally to integrated devices and systems are provided. More particularly, the present invention provides a system and method for integrating MEMS devices with other system applications configured on at least CMOS integrated circuit devices. Merely by way of example, the MEMS devices can include at least a sensor for determining physical perturbations or for determining physical states, such as an accelerometer, a gyroscope, a magnetic sensor, a pressure sensor, a microphone, a humidity sensor, a temperature sensor, a chemical sensor, a biosensor, an inertial sensor, and others. Additionally, the other applications include at least a sensor application or applications, system applications, and broadband applications, among others. But it will be recognized that the invention has a much broader range of applicability.

In one or more embodiments, the present invention provides systems including a sensor processor, applications, and broadband processor, but can also include other applications. In a specific embodiment, the one or more sensor processors are coupled to the one or more application processors. In a specific embodiment, the system is integrated with one or more application processors, one or more baseband processors, and one or more sensor processors coupled to at least two or more MEMS devices. Of course, there can be other variations, modifications, and alternatives.

In a specific embodiment, the present invention provides a sensor processor system on a platform including a semiconductor substrate, e.g., silicon, silicon on insulator, epitaxial silicon. The system has multiple integrated subsystems including a micro controller unit provided on one or more first regions of the semiconductor substrate. The subsystems also include an array of programmable memory provided on one or more second regions of the semiconductor substrate, among other elements. The subsystems also include one or more MEMS devices operably coupled to the micro controller unit. In one or more embodiments, an application processor is coupled to the semiconductor substrate and, optionally, a baseband processor is coupled to the semiconductor substrate.

Many benefits are achieved by way of the present invention over conventional techniques. For example, the present technique provides an easy to use process that relies upon conventional technology. In some embodiments, the method provides higher device yields in dies per wafer with the integrated approach, which has been difficult to achieve. Additionally, the method provides a process and system that are compatible with conventional process technology without substantial modifications to conventional equipment and processes. Preferably, the invention provides for an improved MEMS device system and related applications for a variety of uses. Depending upon the embodiment, one or more of these benefits may be achieved. These and other benefits will be described in more throughout the present specification and more particularly below.

Various additional objects, features and advantages of the present invention can be more fully appreciated with reference to the detailed description and accompanying drawings that follow.

DETAILED DESCRIPTION OF THE INVENTION

According to the present invention, techniques related generally to integrated devices and systems are provided. More particularly, the present invention provides a system and method for integrating MEMS devices with other system applications configured on at least CMOS integrated circuit devices. Merely by way of example, the MEMS devices can include at least an accelerometer, a gyroscope, a magnetic sensor, a pressure sensor, a microphone, a humidity sensor, a temperature sensor, a chemical sensor, a biosensor, an inertial sensor, and others. Additionally, the other applications include at least a sensor application or applications, system applications, and broadband applications, among others. But it will be recognized that the invention has a much broader range of applicability.

Figure 1:
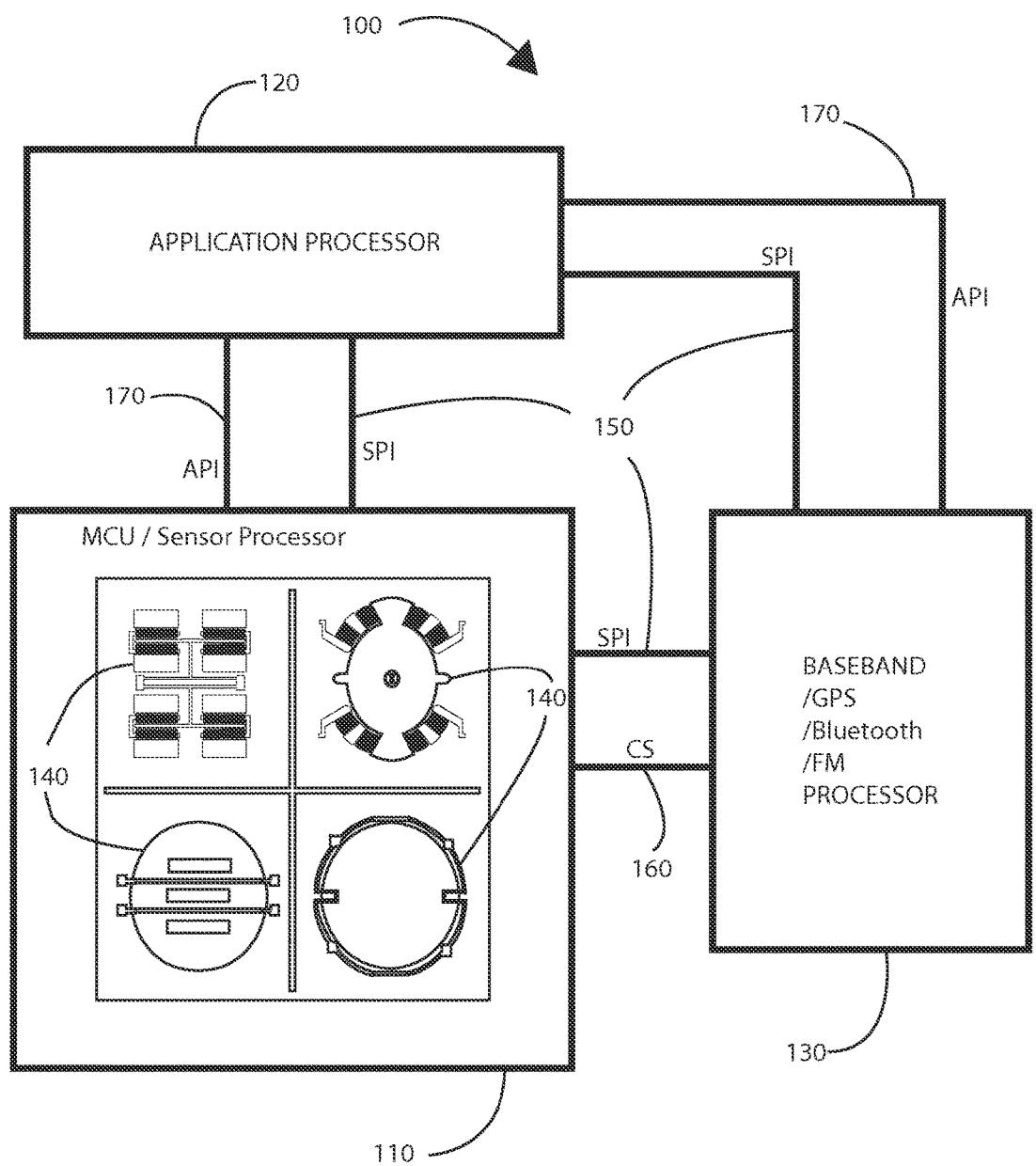
FIG. 1 is a simplified system diagram of a MEMS system according to an embodiment of the present invention.

FIG. 1 is a simplified system diagram of a MEMS system according to an embodiment of the present invention. This diagram is merely an example, which should not unduly limit the scope of the claims herein. One of ordinary skill in the art would recognize other variations, modifications, and alternatives. As shown, the MEMS system 100 includes a sensor processor 110, application(s) processor 120, and broadband/baseband processor 130, in other embodiments, different combinations of processing units can be configured for many different applications. Additionally, one or more of the applications may be combined or each may be separated by one or more sub-applications. For example, each processor can include a single processor, multiple processors, or a number of local or distributed processors operating in parallel or serial or any combination of them. In a specific embodiment, the system 100 is integrated with the one or more application processors 120, which can be coupled to both the one or more sensor processors 110 and the one or more baseband processors 130. Additionally, the one or more sensor processors 110 are coupled to at least two or more MEMS devices 140 in this specific embodiment. Further details of the sensor processors 110 and in particularly the MEMS devices 140 are provided below.

In one or more embodiments, the one or more MEMS devices 140 can be one or more different MEMS, among others. In a specific embodiment, the MEMS 140 is an accelerometer device. An example of an accelerometer device is a three axis accelerometer, but can be other configurations, e.g., single axis, multi-axis, etc. In other embodiments, the MEMS 140 is a gyroscope device, which is a three axis gyroscope, as an example, and other configurations, e.g., single axis, multi-axis, etc. In one or more embodiments, the MEMS 140 can also be a magnetic sensor, a pressure sensor, an rf sensor, an electronic compass, a biosensor, and many others. For example, the MEMS 140 can comprise a three axis accelerometer and a three axis magnetic sensor or a three axis accelerometer and a three axis gyroscope, among other combinations. Alternatively, the MEMS 140 can also comprise a three axis accelerometer, a three axis magnetic sensor, a three axis gyroscope, and a one axis pressure sensor. In addition to the embodiments described here, there can be other variations, modifications, and alternatives. Other examples of MEMS sensor technology can be found in Ljubisa Ristic, ed., "Sensor Technology and Devices," Artech House 1994, ISBN 0-8900-6532-2, which is incorporated herein by reference. Further details regarding the one or more sensor processors 110 and the MEMS devices 140 are described below in FIGS. 2 and 3.

In some embodiments, the system 100 has a processor device such as a micro processor unit (MPU), micro controller unit (MCU), or other programmable controller. In some embodiments, the MCU is configured to output one of a plurality of logic modes, which are respectively associated with a plurality of extrinsic properties, e.g., free fall, tap, specific-axis acceleration, specific-axis deceleration, and rotation. In a specific embodiment, the plurality of logic modes is respectively associated with a plurality of extrinsic properties such that each of the extrinsic properties defines a movement state of an application. In other embodiments, the logic modes may also relate to intrinsic device properties, among others.

In some embodiments, the sensor processors 110 are programmable. In one or more embodiments, the sensor processors 110 comprise an array of programmable memories, e.g., flash, EEPROM, ROM, FPGA. The one or more sensor processors 110 are provided on a general purpose sensor platform. In further embodiments, the sensor processors 110 can include one or more processor devices such as MPUs, MCUs, or other programmable controllers. Other elements including analog front end modules are provided between the two or more MEMS devices and the one or more sensor processors. Further details of the sensor processors can be found throughout the present specification and more particularly below in FIG. 3.

In a specific embodiment, the one or more baseband processors 130 are configured for a variety of wireless communication protocols, such as for GPS, FM, Bluetooth, or Zigbee/Zwave. As used herein, for example, ZigBee generally means, as disclosed by Wikipedia (ZigBee) "a specification for a suite of high level communication protocols using small, low-power digital radios based on the IEEE 802.15.4-2003 standard for wireless personal area networks (WPANs), such as wireless headphones connecting with cell phones via short-range radio." As used herein, as an example, Z-Wave, as disclosed by Wikipedia (Z-Wave), is referred to as "a wireless communications proprietary standard designed for home automation, specifically to remote control applications in residential and light commercial environments." "The technology, which is developed by Sigma Designs' Zensys, uses a low-power RF radio embedded or retrofitted into home electronics devices and systems, such as lighting, home access control, entertainment systems and household appliances . . . [and] has been standardized by the Z-Wave Alliance, an international consortium of manufacturers that oversees interoperability between Z-Wave products and enabled devices." There can also be other interpretations from one of ordinary skill in the art. In one or more embodiments, the baseband processors 130 comprise an array of memories that can store data related the communication protocols and logic modes regarding initiating, manipulating, accessing, or terminating communications data. The one or more broadband processors 130 can be provided on a general purpose communications platform. In further embodiments, the broadband processors 130 can include one or more processor devices such as MPUs, MCUs, or other programmable controllers. Other elements including analog front end modules are provided between the wireless communication devices and the one or more broadband processors. Further details of the broadband processors can be found throughout the present specification and more particularly below in FIG. 4.

In a specific embodiment, the one or more application processors 120 are configured for a variety of information processing applications related to sensor and wireless input data. In one or more embodiments, the applications processors 120 can comprise an array of memories that can store application-specific data related to information processing algorithms, target data, and processed data. The application processors 120 can receive incoming data from and send outgoing data to both the sensor processors 110 and broadband processors 130. In further embodiments, the application processors 120 can include one or more processor devices such as MPUs, MCUs, or other programmable controllers. Of course, there can be other modifications, variations, and alternatives. These application processors 120 can also be provided on a general purpose applications platform, and can also communicate with other processing units via designated data buses.

To communicate between the many subsystems, various interfaces can be used. In one embodiment, the one or more sensor processors are coupled to the one or more baseband processors using both a serial peripheral interface (SPI) bus 150 and a CS interface 160. Additionally, the one or more application processors are coupled to the one or more sensor processors using both an application programming interface (API) bus 170 and a SPI bus 150. In other embodiments, different bus types can be used to replace or augment the function of the serial peripheral 150, application programming 170, and CS 160 interfaces. Those with ordinary skill in the art will recognize the many possibilities of using different subsystems to transfer data between processing components, and electrical buses to transfer electrical signals. Of course, there can be other variations, modifications, and alternatives.

Figure 2:
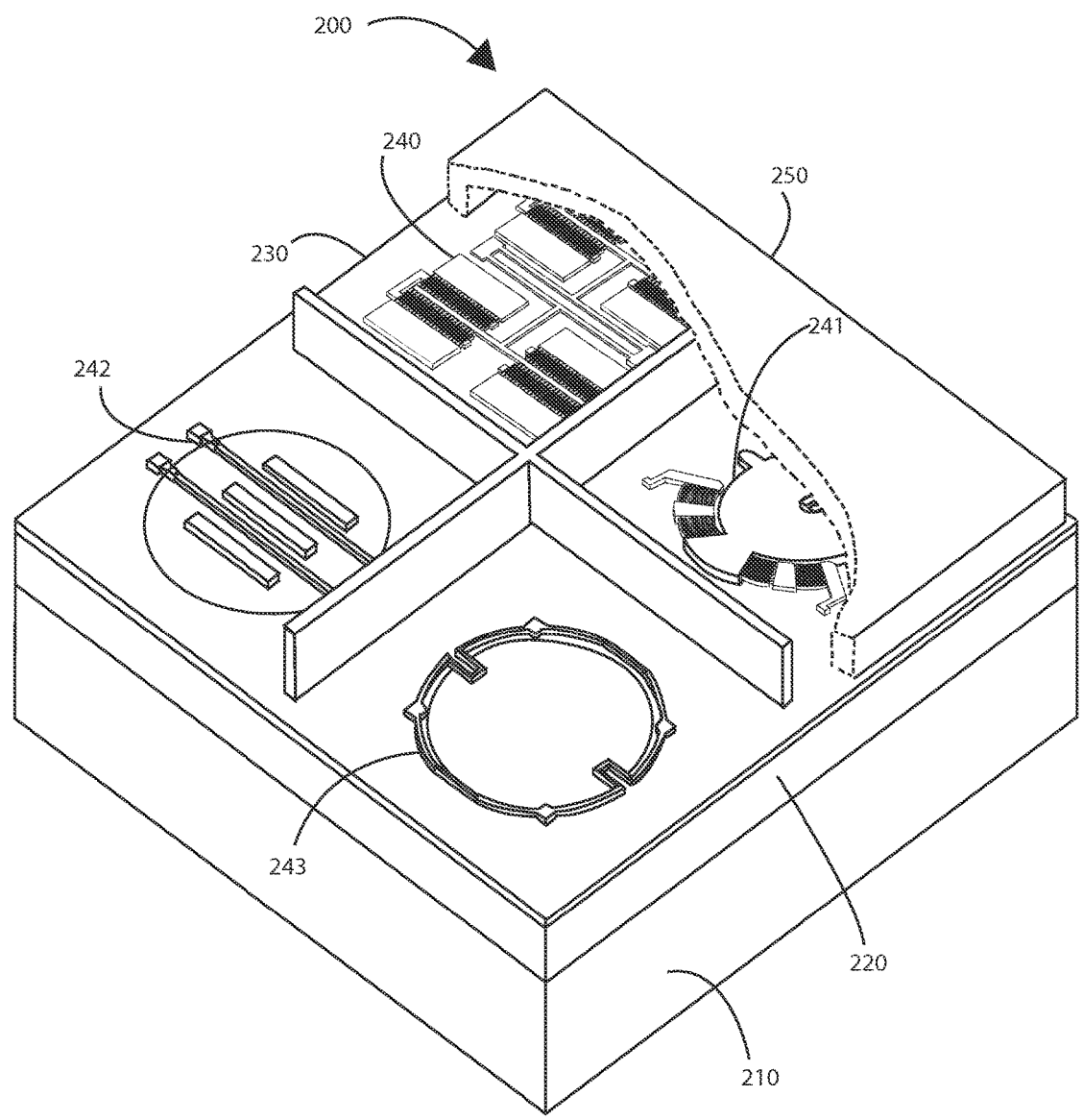
FIG. 2 is a simplified perspective diagram of a MEMS device according to an embodiment of the present invention.

FIG. 2 is a simplified perspective diagram of a MEMS device according to an embodiment of the present invention. This diagram is merely an example, which should not unduly limit the scope of the claims herein. One of ordinary skill in the art would recognize other variations, modifications, and alternatives. As shown, the system 200 includes a substrate layer 210, a semiconductor layer 220, integrated devices 240-243, and an encapsulation layer 250. In a specific embodiment, the each of the devices 240-243 can include a MEMS device; FIG. 2 depicts the integrated system as having an accelerometer 240, a gyroscope 241, a magnetic sensor 242, and a pressure sensor 243. These MEMS devices are integrated with the common semiconductor layer 220 on top of the common substrate layer 210 and are covered by the encapsulation layer 250. In an embodiment, the common semiconductor layer 220 can be made of a silicon material or any other appropriate semiconductor. The semiconductor layer 220 can include a CMOS layer or any other appropriate layer for implementing microelectronics. The CMOS layer 220 creates a surface region which forms an interface region 230, on which the devices 240-243 can be configured. Further details of various integration techniques of the component layers and devices are provided below.

In another embodiment, the MEMS devices 240-243 can include any combination of MEMS devices. These can include accelerometers, gyroscopes, microphones, and sensors. Though not exclusively, the sensors can by any of the following types: magnetic, pressure, humidity, temperature, chemical, biological, or inertial. In further embodiments, any number of MEMS devices can be included in the integrated system 200, and each of these devices can comprise one or more deposited materials, one or more bonded materials, or others. Of course, there can be other variations, modifications, and alternatives.

In another embodiment, the semiconductor layer 220 can include a CMOS layer comprised of any number of metal layers and can be provided on any type of design rule, such as a 0.18 micron design rule or less. Also, the interface region 230 formed by the semiconductor layer can be integrated with any number of CMOS devices, which can be configured from a foundry compatible process. The devices 240-243, and possibly additional devices, can all be configured individually in separate portions of the interface region 230. In further embodiments, the MEMS devices 240-243, and additional devices, and comprise an upper surface region that faces away from the CMOS layer 220 and devices. One skilled in the art would recognize other variations, modifications, and alternatives.

In yet another embodiment, the overlying encapsulation layer 250 can include a chip scale packaging (CSP) layer, such as a wafer level chip scale package (WL-CSP), also known as a wafer level package (WLP). Any other CSP method may be substituted if deemed appropriate by those skilled in the art. Additionally, the CSP layer 250 can be configured to hermetically seal any number of the integrated devices on the interface region 230. Again, there can be many other variations, modifications, and alternatives.

The present technique provides an easy to use process that relies upon conventional technology. This technique can reduce off-chip connections, which makes the mass production of smaller and thinner units possible. Also, integrated CMOS-MEMS technology can achieve high accuracy through the minimization of parasitic resistances and capacitances due to joint fabrication. In some embodiments, the method provides higher device yields in dies per wafer with the integrated approach. Additionally, the method provides a process and system that are compatible with conventional process technology without substantial modifications to conventional equipment and processes.

It is also understood that the examples and embodiments described herein are for illustrative purposes only and that various modifications or changes in light thereof will be suggested to persons skilled in the art and are to be included within the spirit and purview of this application and scope of the appended claims. Further details of the integration of CMOS and MEMS devices can be found throughout the present specification and more particularly below.

Figure 3:
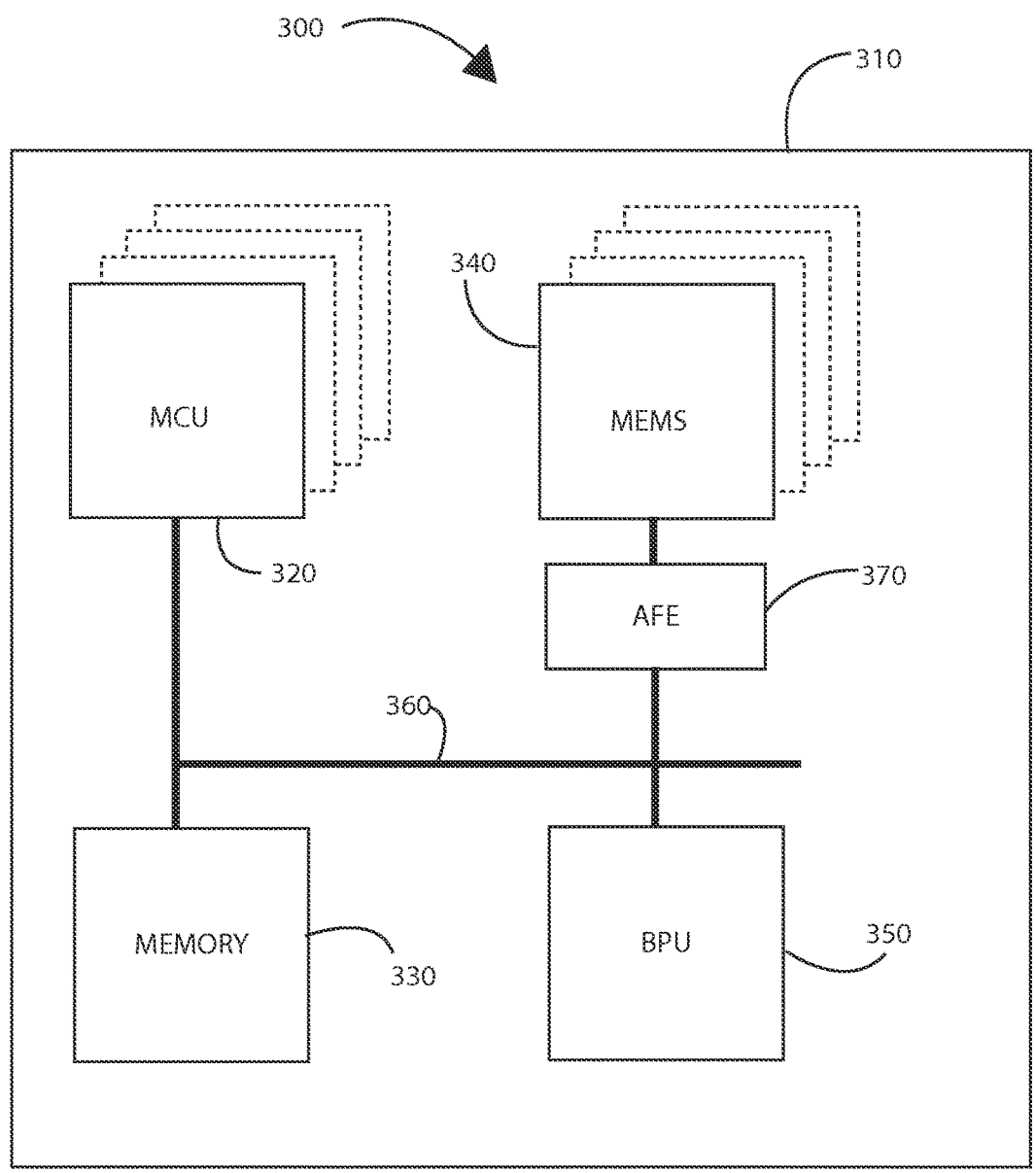
FIG. 3 is a simplified diagram of a sensor processor according to an embodiment of the present invention.

FIG. 3 is a simplified diagram of a sensor processor according to an embodiment of the present invention. This diagram is merely an example, which should not unduly limit the scope of the claims herein. One of ordinary skill in the art would recognize other variations, modifications, and alternatives. As shown, the sensor processor system 300 is provided on a platform including a semiconductor substrate 310 (e.g., silicon, silicon on insulator, epitaxial silicon). The system 300 has multiple integrated subsystems including a processor device 320 such as a micro controller unit that is provided on one or more first regions of the semiconductor substrate 310. The subsystems also include an array of programmable memory 330 provided on one or more second regions of the semiconductor substrate, among other components. The subsystems also include one or more MEMS devices 340 operably coupled to the micro controller unit 320. In one or more embodiments, the application processor 320 is coupled to the semiconductor substrate 310 and, optionally, a baseband processor 350 is coupled to the semiconductor substrate. Of course, there can be other variations, modifications, and alternatives.

In another specific embodiment, the system 300 also uses interface devices 360 to communicate between various subsystems. Depending upon the embodiment, the interface devices can comprise one or more serial peripheral interface (SPI) buses or one or more CS interface buses. Alternatively, the interface devices 360 can comprise one or more application programming interface (API) buses. Depending upon the embodiment, one or more of these interface devices may be combined, used in parallel or serial applications. Again, there can be other variations, modifications, and alternatives.

In one or more embodiments, the one or more MEMS devices 340 can be one or more different MEMS, among others. In a specific embodiment, the MEMS 340 is an accelerometer. An example of an accelerometer is a three axis accelerometer. In other embodiments, the MEMS 340 is a gyroscope, which is a three axis gyroscope, as an example. The MEMS 340 can also be a magnetic sensor, a pressure sensor, among others. In one or more embodiments, the MEMS 340 can comprise a three axis accelerometer and a three axis magnetic sensor. In one or more embodiments, the MEMS 340 can comprise a three axis accelerometer and a three axis gyroscope. Alternatively, the MEMS 340 can comprise a three axis accelerometer, a three axis magnetic sensor, a three axis gyroscope, and a one axis pressure sensor.

In some embodiments, the system 300 has a processor device 320 such as a micro processor unit (MCU), micro controller unit (MCU), or other programmable controller. In some embodiments, the MCU is configured to output one of a plurality of logic modes, which are respectively associated with a plurality of extrinsic properties, e.g., free fall, tap, specific-axis acceleration, specific-axis deceleration, and rotation. In a specific embodiment, the plurality of logic modes is respectively associated with a plurality of extrinsic properties such that each of the extrinsic properties defines a movement state of an application. In other embodiments, intrinsic properties can also be monitored. In another embodiment, the processor unit 320 in the system 300 can include a single processor, multiple processors, or a number of local or distributed processors operating in parallel.

The present system also has one or more analog front end (AFE) modules 370 coupling the MEMS devices 340 and the MCU 320. In some embodiments, each of the analog front end modules 370 is configured to process one or more signals from the one or more sensor devices, amplify and/or filter the signals, if desired, and transfer the signals. An example of the analog front end 370 is an analog to digital (ADC) converter device, but can be others. More preferably, the MEMS devices 340 are coupled to an analog front end 370, which is coupled to an amplifier. In one or more embodiments, the amplifier is coupled to an ADC converter device 370, which is coupled to the MCU 320. Of course, there can be other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 4:
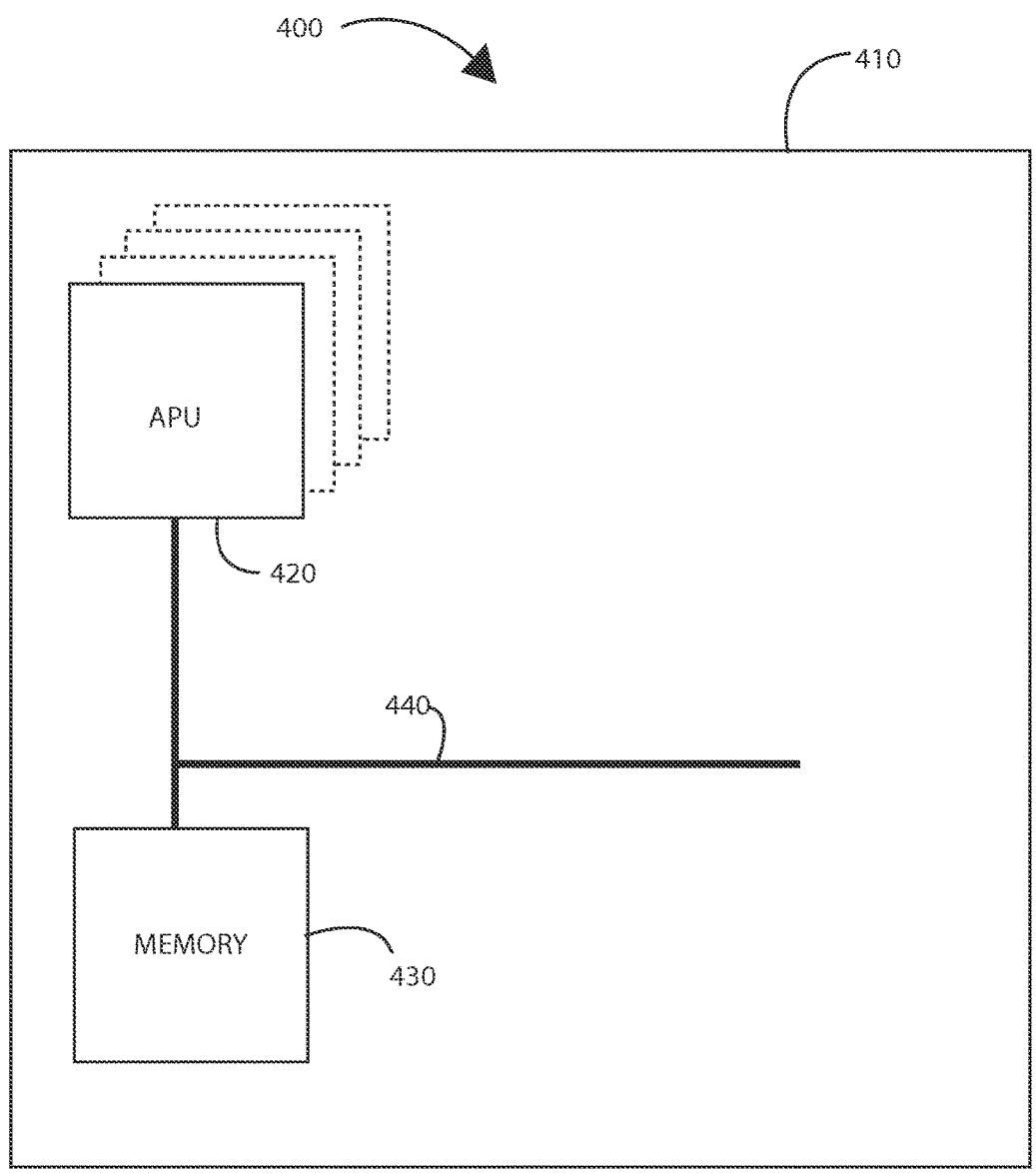
FIG. 4 is a simplified diagram of an application processor according to an embodiment of the present invention.

FIG. 4 is a simplified diagram of an application processor according to an embodiment of the present invention. This diagram is merely an example, which should not unduly limit the scope of the claims herein. One of ordinary skill in the art would recognize other variations, modifications, and alternatives. As shown, the application processor system 400 is provided on a platform including a semiconductor substrate 410 (e.g., silicon, silicon on insulator, epitaxial silicon). The system 400 has multiple integrated subsystems including a processor device 420 such as an application processor unit (APU) that is provided on one or more first regions of the semiconductor substrate 410. The subsystems also include an array of memory 430 provided on one or more second regions of the semiconductor substrate, among other components. In one or more embodiments, the application processor 420 is coupled to the semiconductor substrate 410 along with other processor units. Of course, there can be other variations, modifications, and alternatives.

In another specific embodiment, the system 400 also uses interface devices 440 to communicate between various subsystems. Depending upon the embodiment, the interface devices can comprise one or more serial peripheral interface (SPI) buses or one or more CS interface buses. Alternatively, the interface devices 440 can comprise one or more application programming interface (API) buses. Depending upon the embodiment, one or more of these interface devices may be combined, used in parallel or serial applications. Of course, there can be other variations, modifications, and alternatives.

In a specific embodiment, the one or more application processors 420 are configured for a variety of information processing applications related to sensor and wireless input data. In one or more embodiments, the applications processor system 400 can comprise an array of memories 430 that can store application-specific data related to information processing algorithms, target data, and processed data. The application processors 420 can receive incoming data from and send outgoing data to both the sensor processors and broadband processors. In further embodiments, the application processors 420 can include one or more processor devices such as APUs, MPUs, MCUs, or other programmable controllers. Of course, there can be other modifications, variations, and alternatives. These application processors 420 can also be provided on a general purpose applications platform, and can also communicate with other processing units via designated data buses.

It is also understood that the examples and embodiments described herein are for illustrative purposes only and that various modifications or changes in light thereof will be suggested to persons skilled in the art and are to be included within the spirit and purview of this application and scope of the appended claims.

Figure 5:
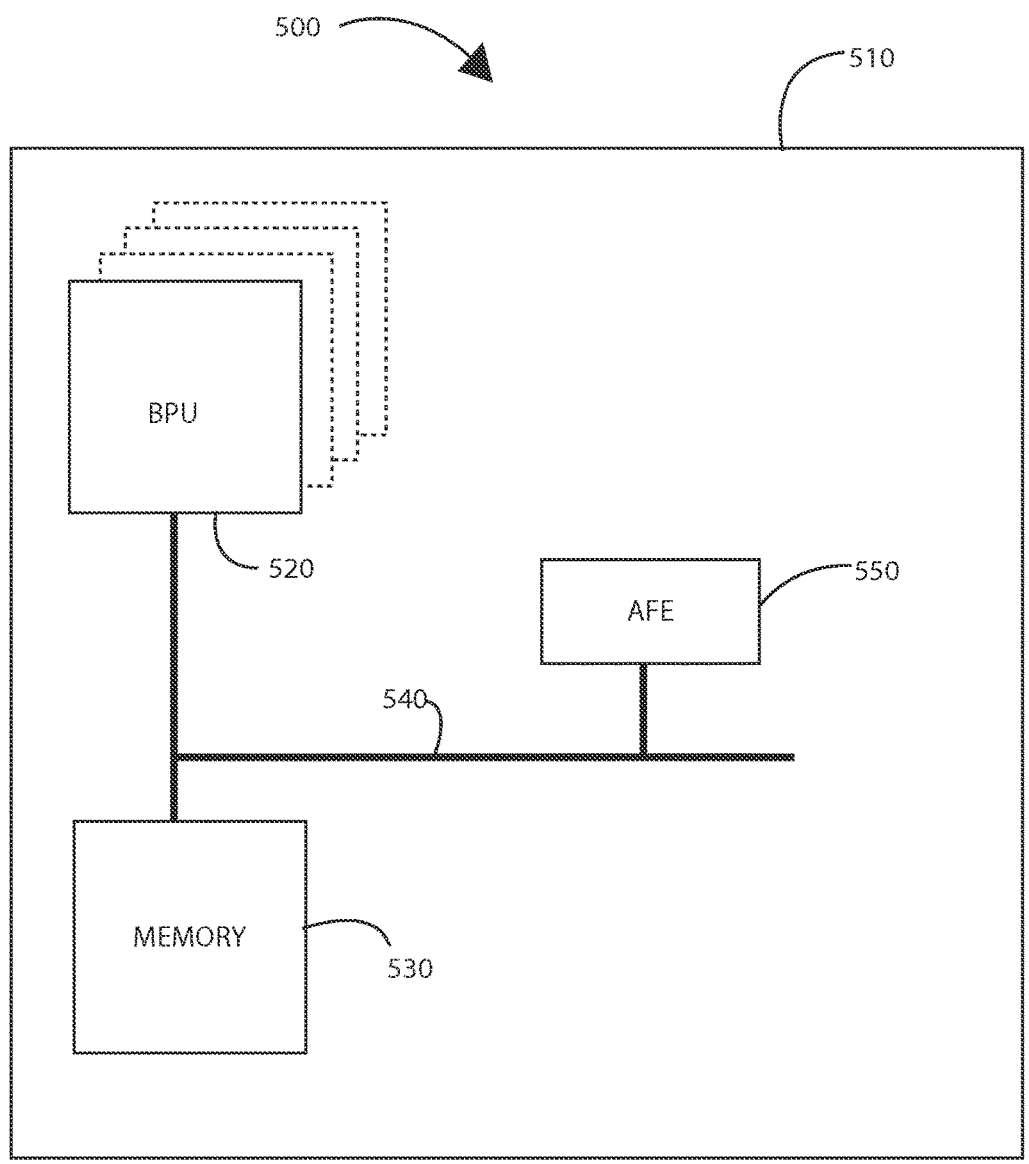
FIG. 5 is a simplified diagram of a broadband processor according to an embodiment of the present invention.

FIG. 5 is a simplified diagram of a broadband processor according to an embodiment of the present invention. This diagram is merely an example, which should not unduly limit the scope of the claims herein. One of ordinary skill in the art would recognize other variations, modifications, and alternatives. As shown, the broadband processor system 500 is provided on a platform including a semiconductor substrate 510 (e.g., silicon, silicon on insulator, epitaxial silicon). The system 500 has multiple integrated subsystems including a processor device 520 such as a broadband processor unit (BPU) that is provided on one or more first regions of the semiconductor substrate 510. The subsystems also include an array of memory 530 provided on one or more second regions of the semiconductor substrate, among other components. In one or more embodiments, the broadband processor 520 is coupled to the semiconductor substrate 510 along with other processor units. Of course, there can be other variations, modifications, and alternatives.

In another specific embodiment, the system 500 also uses interface devices 540 to communicate between various subsystems. Depending upon the embodiment, the interface devices can comprise one or more serial peripheral interface (SPI) buses or one or more CS interface buses. Alternatively, the interface devices 540 can comprise one or more application programming interface (API) buses. Depending upon the embodiment, one or more of these interface devices may be combined, used in parallel or serial applications. The present system 500 also has one or more analog front end (AFE) modules 550 coupling the BPU 520 to external communications devices. An example of the analog front end 550 is an analog to digital (ADC) converter device, but can be others. Of course, there can be other variations, modifications, and alternatives.

In a specific embodiment, the one or more baseband processors 520 are configured for a variety of wireless communication protocols, such as for GPS, FM, Bluetooth, or Zigbee/Zwave. Those skilled in the art will recognize the use of many other wireless sensor networks (WSN) for system-on-chip (SOC) applications. In one or more embodiments, the baseband processors 520 comprise an array of memories 530 that can store data related the communication protocols and logic modes regarding initiating, manipulating, accessing, or terminating communications data. The one or more broadband processors 520 can be provided on a general purpose communications platform. In further embodiments, the broadband processors 520 can include one or more processor devices such as MPUs, MCUs, or other programmable controllers. Other elements including analog front end modules 550 are provided between the wireless communication devices and the one or more broadband processors 520.

It is also understood that the examples and embodiments described herein are for illustrative purposes only and that various modifications or changes in light thereof will be suggested to persons skilled in the art and are to be included within the spirit and purview of this application and scope of the appended claims.

Figure 6:
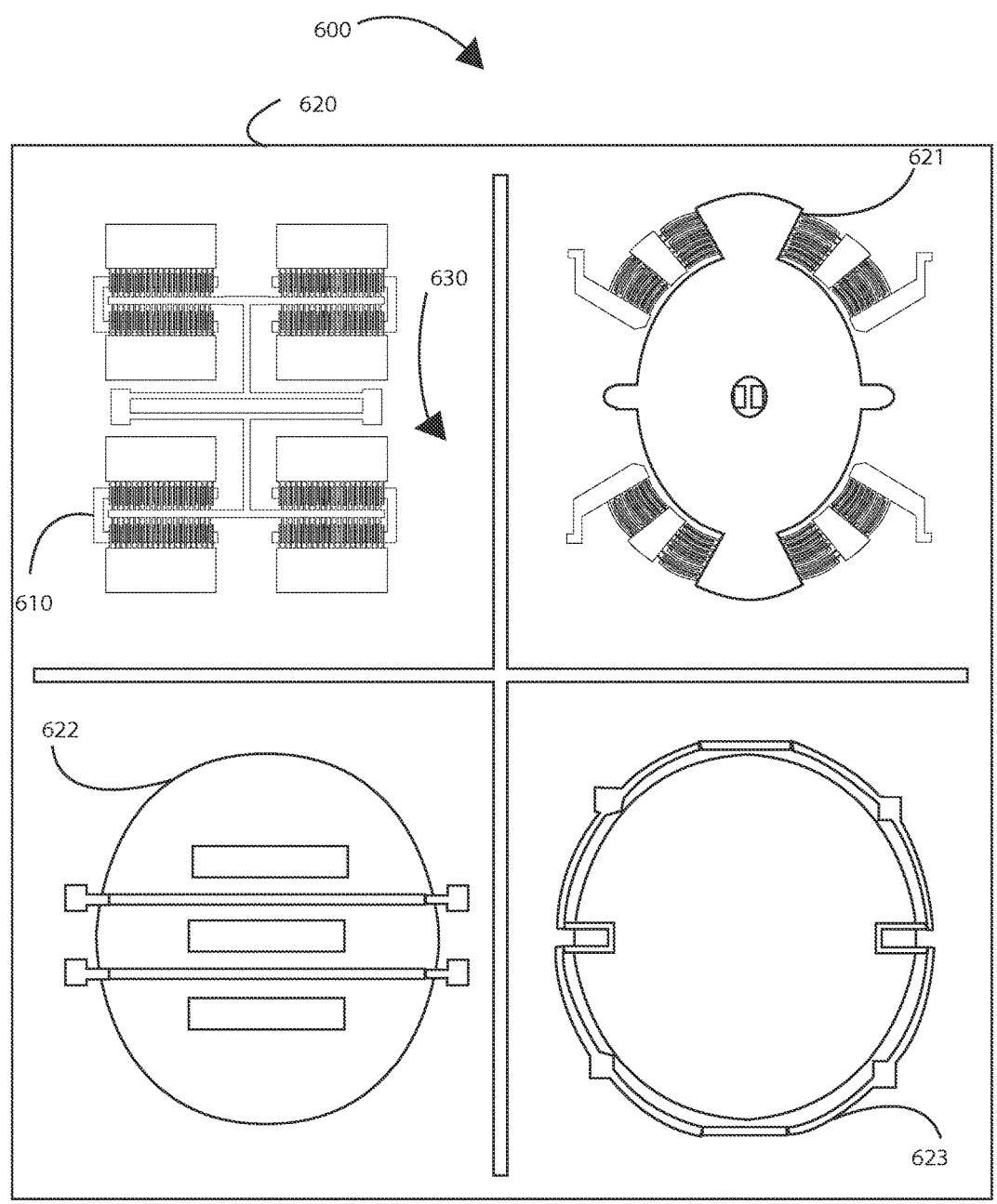
FIG. 6 is a simplified top diagram of a MEMS device according to an embodiment of the present invention.

FIG. 6 is a simplified top diagram of a MEMS device according to an embodiment of the present invention. This diagram is merely an example, which should not unduly limit the scope of the claims herein. One of ordinary skill in the art would recognize other variations, modifications, and alternatives. As shown, the system 600 includes a semiconductor layer 610, devices 620-623, and an interface region 630. Of course, there can be other variations, modifications, and alternatives. In a specific embodiment, the each of the devices 620-623 can include a MEMS device; FIG. 2 depicts the integrated system 600 as having an accelerometer 620, a gyroscope 621, a magnetic sensor 622, and a pressure sensor 623. These MEMS devices are integrated with the common semiconductor layer 610. In an embodiment, the common semiconductor layer 610 can be made of a silicon material or any other appropriate semiconductor. The semiconductor layer 610 can include a CMOS layer or any other appropriate layer for implementing microelectronics. The CMOS layer 610 creates a surface region which forms an interface region 630, on which the devices 620-623 can be configured.

In another embodiment, the MEMS devices 620-623 can include any combination of MEMS devices. These can include accelerometers, gyroscopes, microphones, and sensors. Though not exclusively, the sensors can by any of the following types: magnetic, pressure, humidity, temperature, chemical, biological, or inertial. In further embodiments, any number of MEMS devices can be included in the integrated system 600, and each of these devices can comprise one or more deposited materials, one or more bonded materials, or others. Of course, there can be other variations, modifications, and alternatives.

In another embodiment, the semiconductor layer 610 can include a CMOS layer comprised of any number of metal layers and can be provided on any type of design rule, such as a 0.18 micron design rule or less. Also, the interface region 630 formed by the semiconductor layer can be integrated with any number of CMOS devices, which can be configured from a foundry compatible process. The devices 620-623, and possibly additional devices, can all be configured individually in separate portions of the interface region 630. In further embodiments, the MEMS devices 620-623, and additional devices, and comprise an upper surface region that faces away from the CMOS layer 610 and devices. One skilled in the art would recognize other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 7:
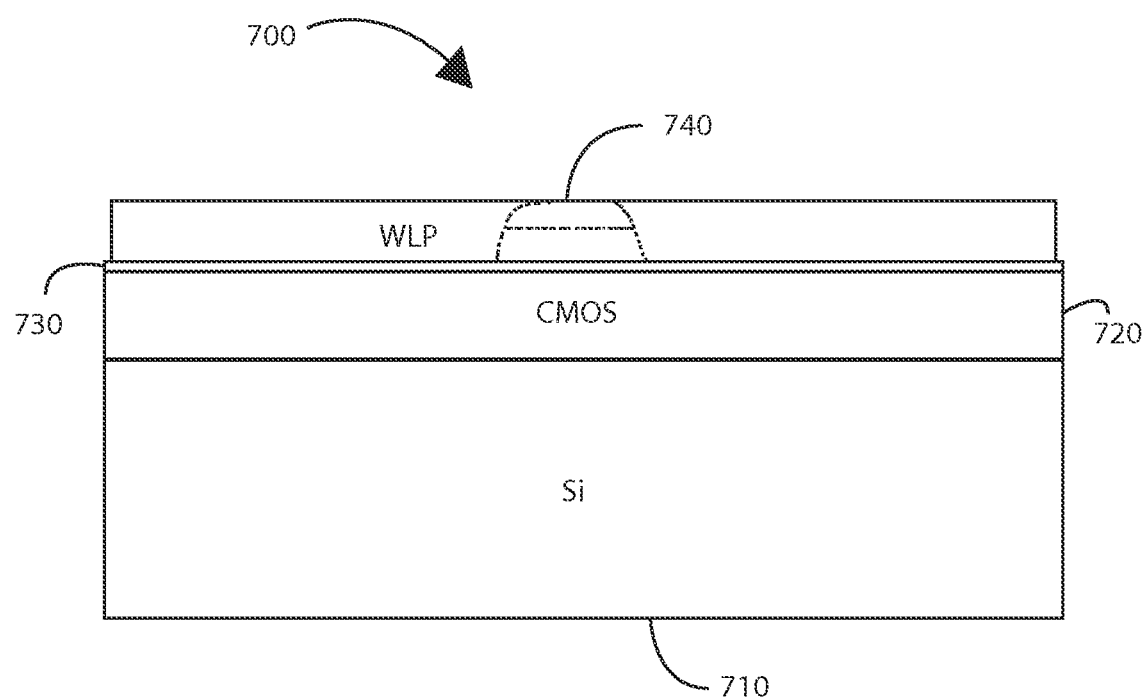
FIG. 7 is a simplified side diagram of a MEMS device according to an embodiment of the present invention.

FIG. 7 is a simplified side diagram of a MEMS device according to an embodiment of the present invention. This diagram is merely an example, which should not unduly limit the scope of the claims herein. One of ordinary skill in the art would recognize other variations, modifications, and alternatives. As shown, the system 700 includes a substrate layer 710, a semiconductor layer 720, and an encapsulation layer 740. The semiconductor layer 720 covers the substrate layer 710 while also creating a surface region that forms an interface region 730. In an embodiment, the common semiconductor layer 720 can be made of a silicon material or any other appropriate semiconductor. The semiconductor layer 720 can include a CMOS layer or any other appropriate layer for implementing microelectronics.

In another embodiment, the semiconductor layer 720 can include a CMOS layer comprised of any number of metal layers and can be provided on any type of design rule, such as a 0.18 micron design rule or less. Also, the interface region 730 formed by the semiconductor layer can be integrated with any number of MEMS devices and CMOS devices; the CMOS devices can be configured from a foundry compatible process. The CMOS and MEMS devices can all be configured individually in separate portions of the interface region 730. One skilled in the art would recognize other variations, modifications, and alternatives.

In yet another embodiment, the overlying encapsulation layer 740 can include a chip scale packaging (CSP) layer, such as a wafer level chip scale package (WL-CSP), also known as a wafer level package (WLP). Any other CSP method may be substituted if deemed appropriate by those skilled in the art. Additionally, the CSP layer 740 can be configured to hermetically seal any number of the integrated devices on the interface region 730. Again, there can be many other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 8:
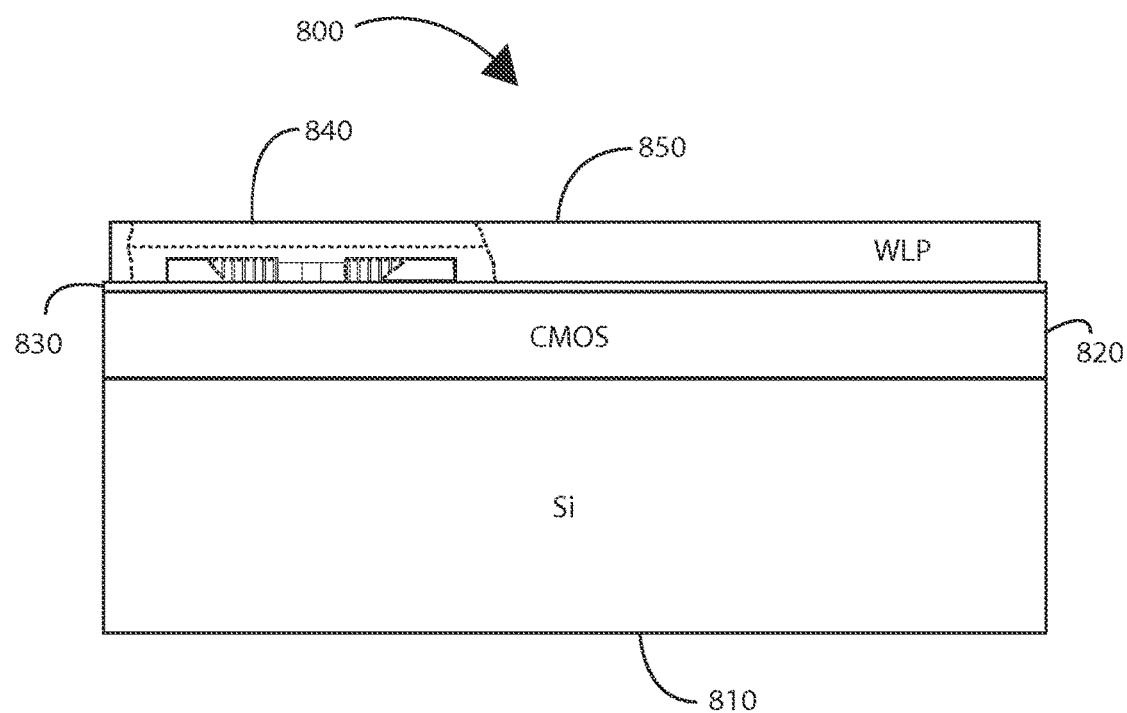
FIG. 8 is a simplified side diagram of a MEMS device according to another embodiment of the present invention.

FIG. 8 is a simplified side diagram of a MEMS device according to another embodiment of the present invention. This diagram is merely an example, which should not unduly limit the scope of the claims herein. One of ordinary skill in the art would recognize other variations, modifications, and alternatives. As shown, the system 800 includes a substrate layer 810, a semiconductor layer 820, an integrated device 840, and an encapsulation layer 850. The semiconductor layer 820 covers the substrate layer 810 while also creating a surface region that forms an interface region 830. In an embodiment, the common semiconductor layer 820 can be made of a silicon material or any other appropriate semiconductor. The semiconductor layer 820 can include a CMOS layer or any other appropriate layer for implementing microelectronics.

In another embodiment, the semiconductor layer 820 can include a CMOS layer comprised of any number of metal layers and can be provided on any type of design rule, such as a 0.18 micron design rule or less. Also, the interface region 830 formed by the semiconductor layer can be integrated with any number of MEMS devices and CMOS devices; the CMOS devices can be configured from a foundry compatible process. The CMOS and MEMS devices can all be configured individually in separate portions of the interface region 830. One skilled in the art would recognize other variations, modifications, and alternatives.

In a specific embodiment, the integrated device 840 can be an accelerometer. In further embodiments, any number of MEMS devices can be included in the integrated system 800, and each of these devices can comprise one or more deposited materials, one or more bonded materials, or others. Of course, there can be other variations, modifications, and alternatives.

In yet another embodiment, the overlying encapsulation layer 840 can include a chip scale packaging (CSP) layer, such as a wafer level chip scale package (WL-CSP), also known as a wafer level package (WLP). Any other CSP method may be substituted if deemed appropriate by those skilled in the art. Additionally, the CSP layer 840 can be configured to hermetically seal any number of the integrated devices on the interface region 830. Again, there can be many other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 9:
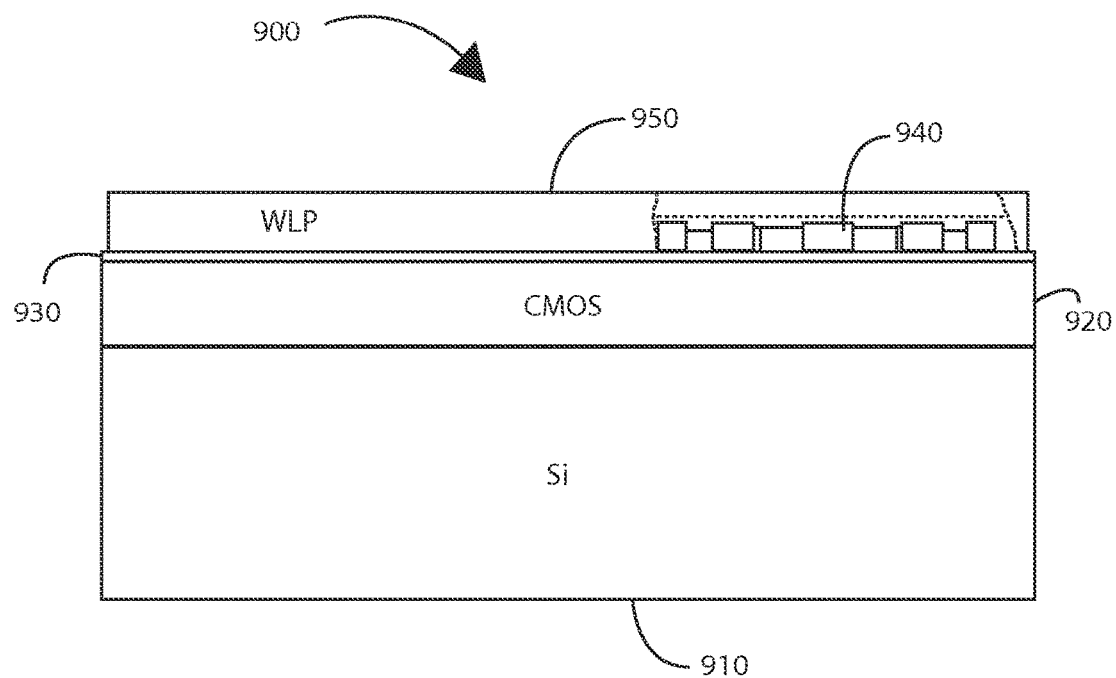
FIG. 9 is a simplified side diagram of a MEMS device according to yet another embodiment of the present invention.

FIG. 9 is a simplified side diagram of a MEMS device according to yet another embodiment of the present invention. This diagram is merely an example, which should not unduly limit the scope of the claims herein. One of ordinary skill in the art would recognize other variations, modifications, and alternatives. As shown, the system 900 includes a substrate layer 910, a semiconductor layer 920, an integrated device 940, and an encapsulation layer 950. The semiconductor layer 920 covers the substrate layer 910 while also creating a surface region that forms an interface region 930. In an embodiment, the common semiconductor layer 920 can be made of a silicon material or any other appropriate semiconductor. The semiconductor layer 920 can include a CMOS layer or any other appropriate layer for implementing microelectronics.

In another embodiment, the semiconductor layer 920 can include a CMOS layer comprised of any number of metal layers and can be provided on any type of design rule, such as a 0.18 micron design rule or less. Also, the interface region 930 formed by the semiconductor layer can be integrated with any number of MEMS devices and CMOS devices; the CMOS devices can be configured from a foundry compatible process. The CMOS and MEMS devices can all be configured individually in separate portions of the interface region 930. One skilled in the art would recognize other variations, modifications, and alternatives.

In a specific embodiment, the integrated device 940 can be a gyroscope. In further embodiments, any number of MEMS devices can be included in the integrated system 900, and each of these devices can comprise one or more deposited materials, one or more bonded materials, or others. Of course, there can be other variations, modifications, and alternatives.

In yet another embodiment, the overlying encapsulation layer 940 can include a chip scale packaging (CSP) layer, such as a wafer level chip scale package (WL-CSP), also known as a wafer level package (WLP). Any other CSP method may be substituted if deemed appropriate by those skilled in the art. Additionally, the CSP layer 940 can be configured to hermetically seal any number of the integrated devices on the interface region 930. Again, there can be many other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 10:
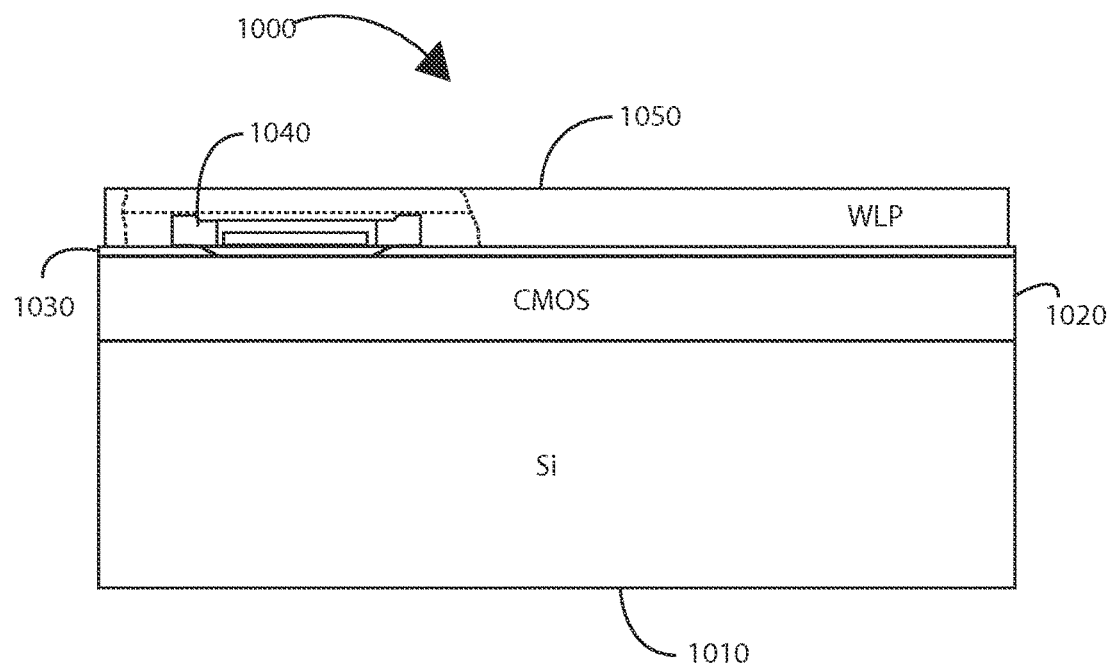
FIG. 10 is a simplified side diagram of a MEMS device according to yet another embodiment of the present invention.

FIG. 10 is a simplified side diagram of a MEMS device according to yet another embodiment of the present invention. This diagram is merely an example, which should not unduly limit the scope of the claims herein. One of ordinary skill in the art would recognize other variations, modifications, and alternatives. As shown, the system 1000 includes a substrate layer 1010, a semiconductor layer 1020, an integrated device 1040, and an encapsulation layer 1050. The semiconductor layer 1020 covers the substrate layer 1010 while also creating a surface region that forms an interface region 1030. In an embodiment, the common semiconductor layer 1020 can be made of a silicon material or any other appropriate semiconductor. The semiconductor layer 1020 can include a CMOS layer or any other appropriate layer for implementing microelectronics.

In another embodiment, the semiconductor layer 1020 can include a CMOS layer comprised of any number of metal layers and can be provided on any type of design rule, such as a 0.18 micron design rule or less. Also, the interface region 1030 formed by the semiconductor layer can be integrated with any number of MEMS devices and CMOS devices; the CMOS devices can be configured from a foundry compatible process. The CMOS and MEMS devices can all be configured individually in separate portions of the interface region 1030. One skilled in the art would recognize other variations, modifications, and alternatives.

In a specific embodiment, the integrated device 1040 can be a magnetic sensor. In further embodiments, any number of MEMS devices can be included in the integrated system 1000, and each of these devices can comprise one or more deposited materials, one or more bonded materials, or others. Of course, there can be other variations, modifications, and alternatives.

In yet another embodiment, the overlying encapsulation layer 1040 can include a chip scale packaging (CSP) layer, such as a wafer level chip scale package (WL-CSP), also known as a wafer level package (WLP). Any other CSP method may be substituted if deemed appropriate by those skilled in the art. Additionally, the CSP layer 1040 can be configured to hermetically seal any number of the integrated devices on the interface region 1030. Again, there can be many other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 11:
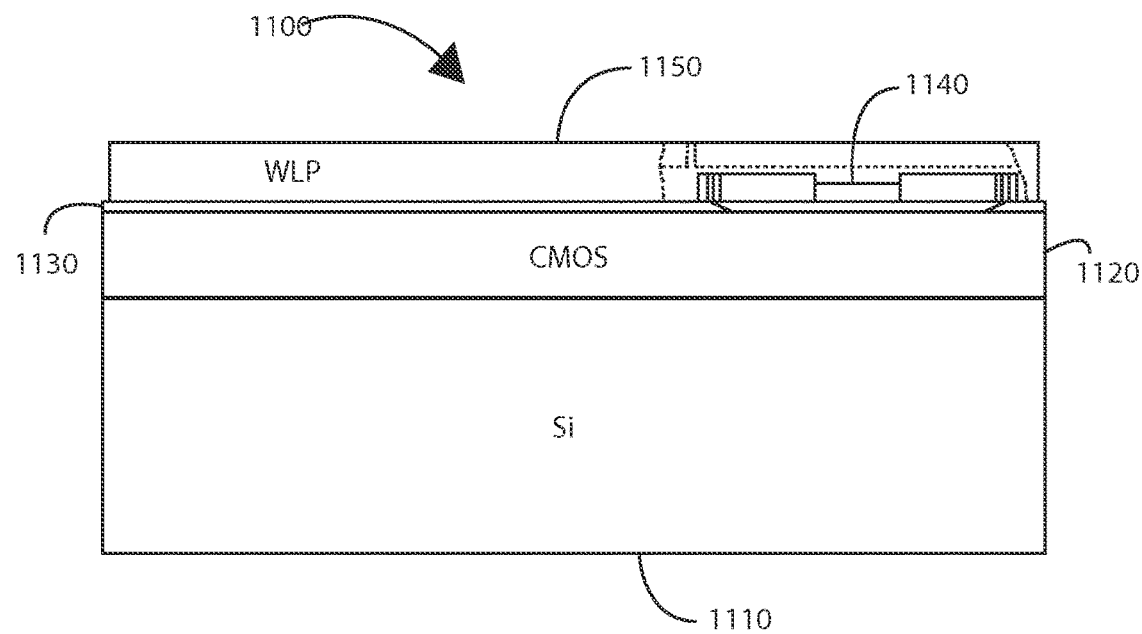
FIG. 11 is a simplified side diagram of a MEMS device according to yet another embodiment of the present invention.

FIG. 11 is a simplified side diagram of a MEMS device according to yet another embodiment of the present invention. This diagram is merely an example, which should not unduly limit the scope of the claims herein. One of ordinary skill in the art would recognize other variations, modifications, and alternatives. As shown, the system 1100 includes a substrate layer 1110, a semiconductor layer 1120, an integrated device 1140, and an encapsulation layer 1150. The semiconductor layer 1120 covers the substrate layer 1110 while also creating a surface region that forms an interface region 1130. In an embodiment, the common semiconductor layer 1120 can be made of a silicon material or any other appropriate semiconductor. The semiconductor layer 1120 can include a CMOS layer or any other appropriate layer for implementing microelectronics.

In another embodiment, the semiconductor layer 1120 can include a CMOS layer comprised of any number of metal layers and can be provided on any type of design rule, such as a 0.18 micron design rule or less. Also, the interface region 1130 formed by the semiconductor layer can be integrated with any number of MEMS devices and CMOS devices; the CMOS devices can be configured from a foundry compatible process. The CMOS and MEMS devices can all be configured individually in separate portions of the interface region 1130. One skilled in the art would recognize other variations, modifications, and alternatives.

In a specific embodiment, the integrated device 1140 can be a pressure sensor. In further embodiments, any number of MEMS devices can be included in the integrated system 700, and each of these devices can comprise one or more deposited materials, one or more bonded materials, or others. Of course, there can be other variations, modifications, and alternatives.

In yet another embodiment, the overlying encapsulation layer 1140 can include a chip scale packaging (CSP) layer, such as a wafer level chip scale package (WL-CSP), also known as a wafer level package (WLP). Any other CSP method may be substituted if deemed appropriate by those skilled in the art. Additionally, the CSP layer 1140 can be configured to hermetically seal any number of the integrated devices on the interface region 1130. Again, there can be many other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 12:
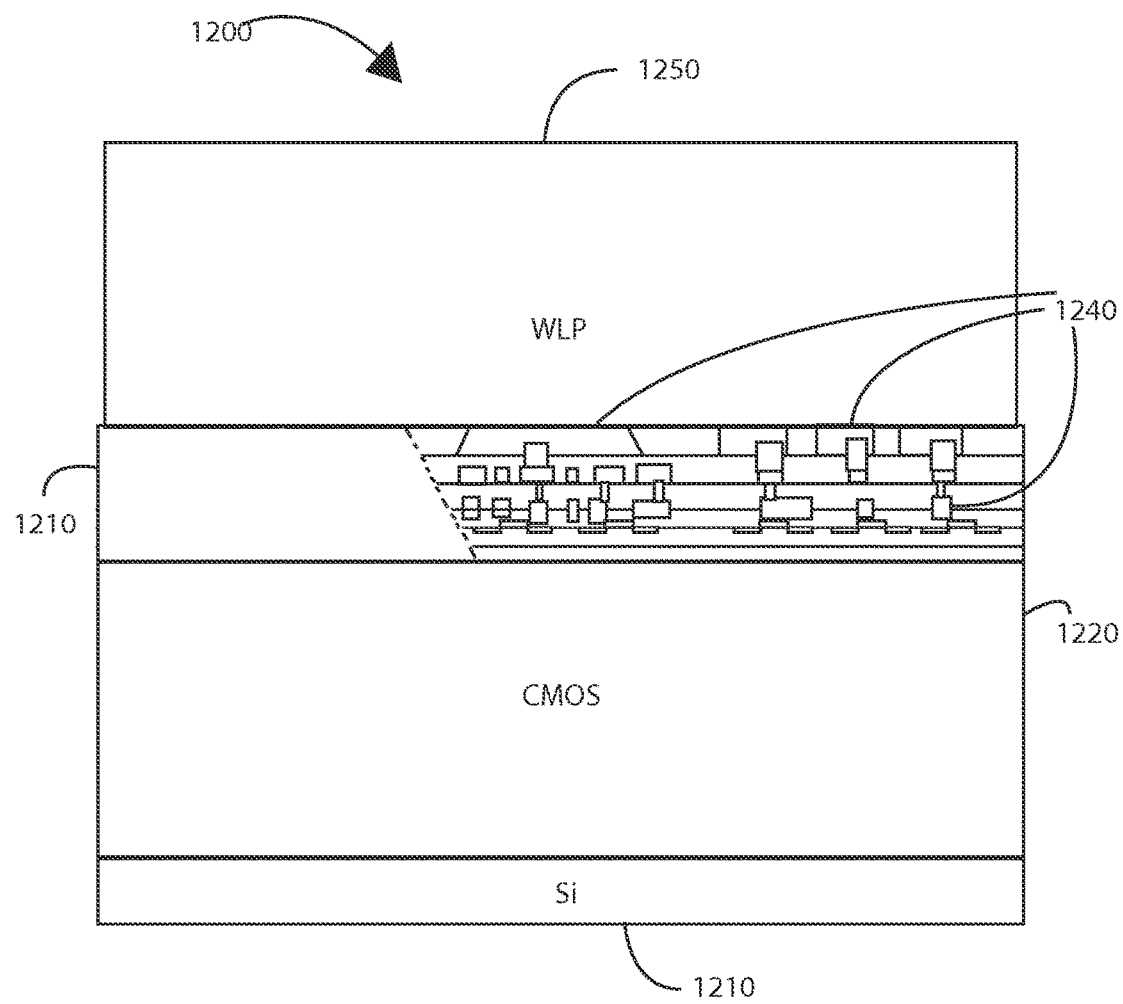
FIG. 12 is a simplified side diagram of a MEMS device according to yet another embodiment of the present invention.

FIG. 12 is a simplified side diagram of a MEMS device according to yet another embodiment of the present invention. This diagram is merely an example, which should not unduly limit the scope of the claims herein. One of ordinary skill in the art would recognize other variations, modifications, and alternatives. As shown, the system 1200 includes a substrate layer 1210, a semiconductor layer 1220, a CMOS device 1240, and an encapsulation layer 1250. The semiconductor layer 1220 covers the substrate layer 1210 while also creating a surface region that forms an interface region 1230. In an embodiment, the common semiconductor layer 1220 can be made of a silicon material or any other appropriate semiconductor. The semiconductor layer 1220 can include a CMOS layer or any other appropriate layer for implementing microelectronics.

Figure 14:
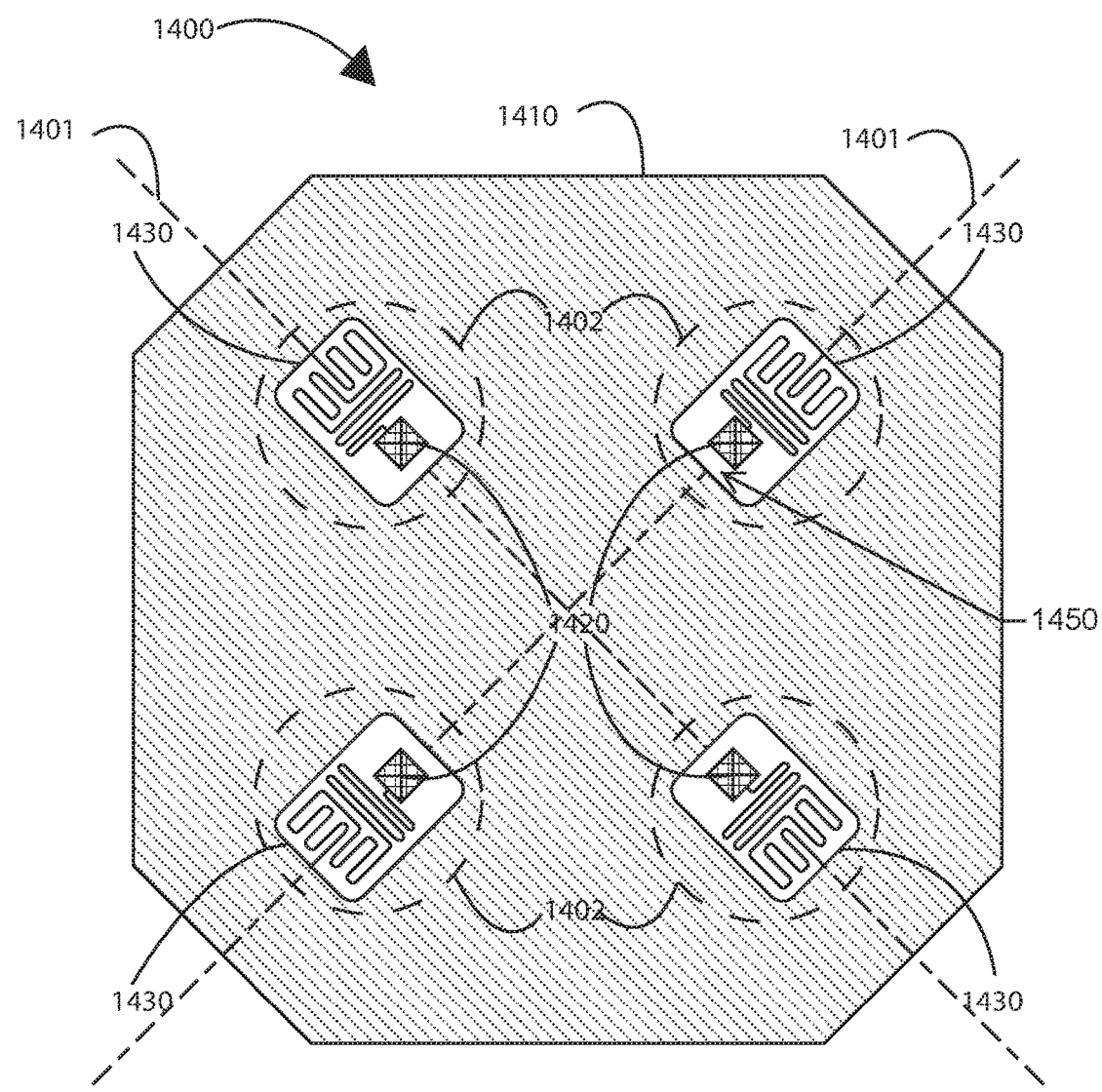
FIG. 14 is a simplified top diagram of a component of an integrated CMOS-MEMS system according to an embodiment of the present invention.
Figure 15:
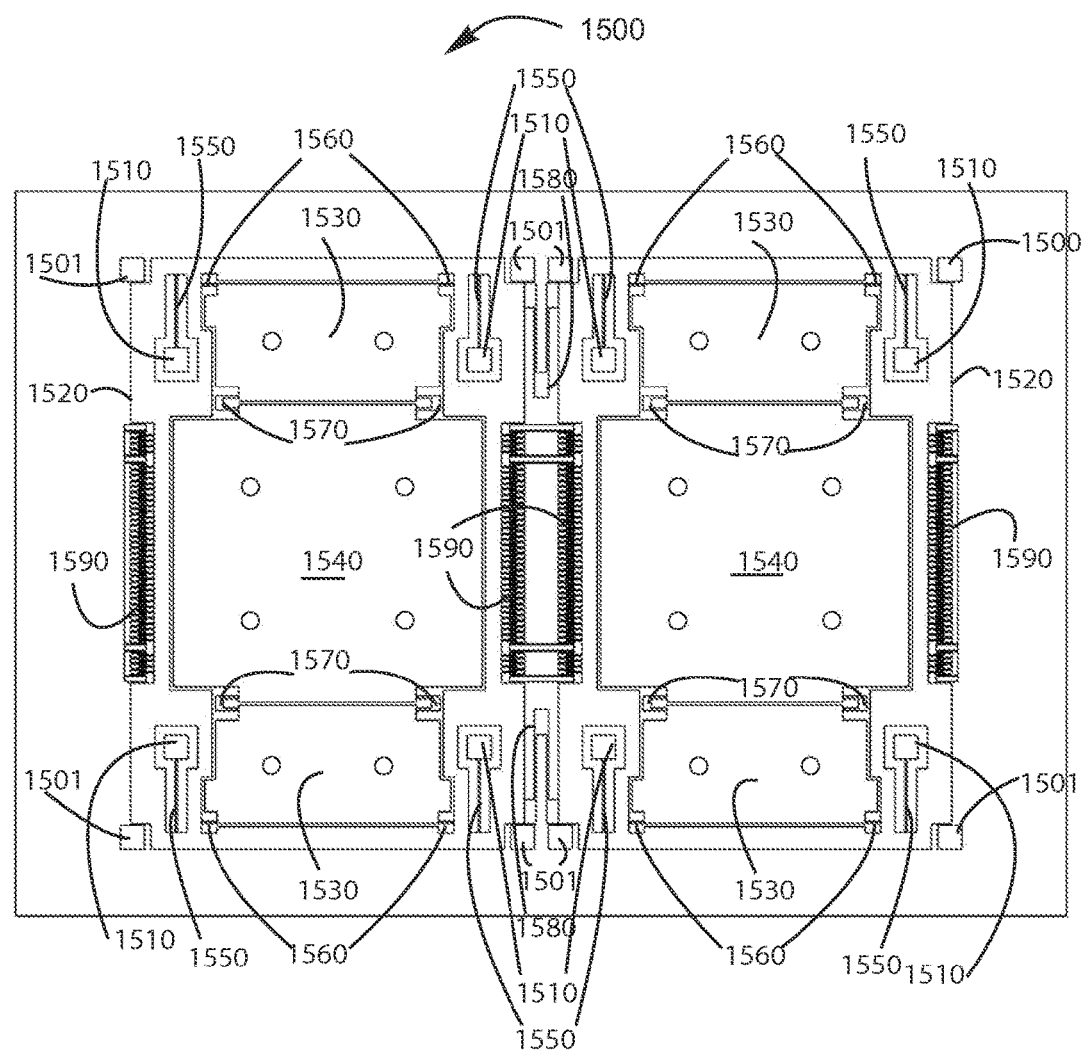
FIG. 15 is a simplified top diagram of a component of an integrated CMOS-MEMS system according to an embodiment of the present invention.
Figure 16:
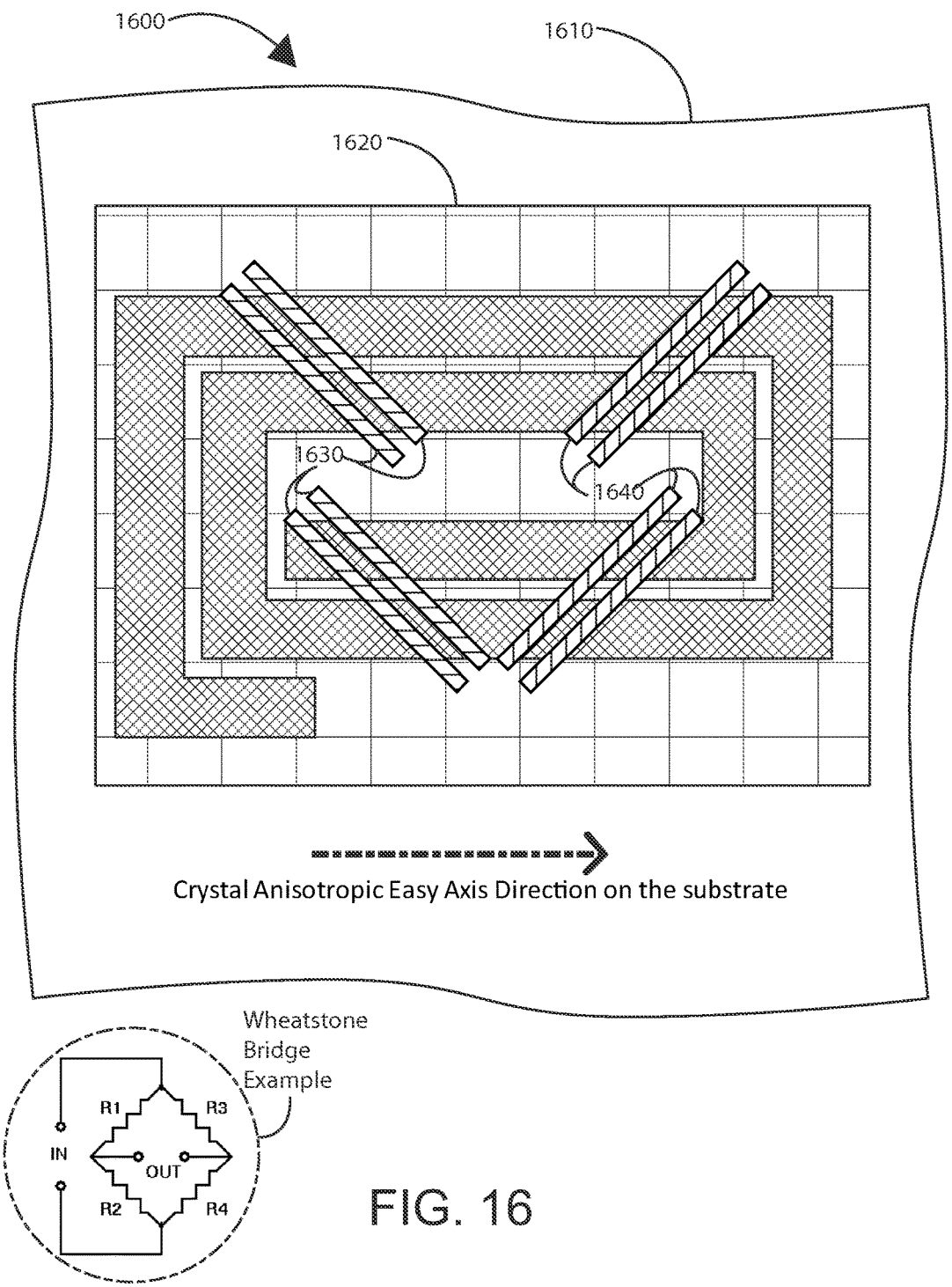
FIG. 16 is a simplified top diagram of a component of an integrated CMOS-MEMS system according to an embodiment of the present invention.

In another embodiment, the semiconductor layer 1220 can include a CMOS layer comprised of any number of metal layers and can be provided on any type of design rule, such as a 0.18 micron design rule or less. The CMOS device 1240 can be integrated into the CMOS layer 1220 and configured with the interface region 1230. Also, the CMOS device 1240 can be configured from a foundry compatible process. Also, the interface region 1230 formed by the semiconductor layer can be integrated with any number of MEMS devices and CMOS devices; the CMOS devices can be configured from a foundry compatible process. In various embodiments, any number of MEMS devices may be fabricated substantially simultaneously upon interface region 1230. For example, MEMS devices may or may not be patterned using the same masks as other MEMS devices, MEMS devices may or may not be fabricated using deposited material that is used for other MEMS devices, MEMS devices may or may not be fabricated using the same process steps that are used to fabricate other MEMS devices, or the like. Using such embodiments, more than one different MEMS device-type can be fabricated upon interface region 1230 in parallel, thus saving time compared to serial fabrication of such MEMS devices. FIGS. 14-16 illustrate an example of some of the MEMS devices that can be fabricated approximately in parallel using the techniques described above. The CMOS and MEMS devices can all be configured individually in separate portions of the interface region 1230. One skilled in the art would recognize other variations, modifications, and alternatives.

In yet another embodiment, the overlying encapsulation layer 1250 can include a chip scale packaging (CSP) layer, such as a wafer level chip scale package (WL-CSP), also known as a wafer level package (WLP). Any other CSP method may be substituted if deemed appropriate by those skilled in the art. Additionally, the CSP layer 1250 can be configured to hermetically seal any number of the integrated devices on the interface region 1230. Again, there can be many other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

Figure 13A:
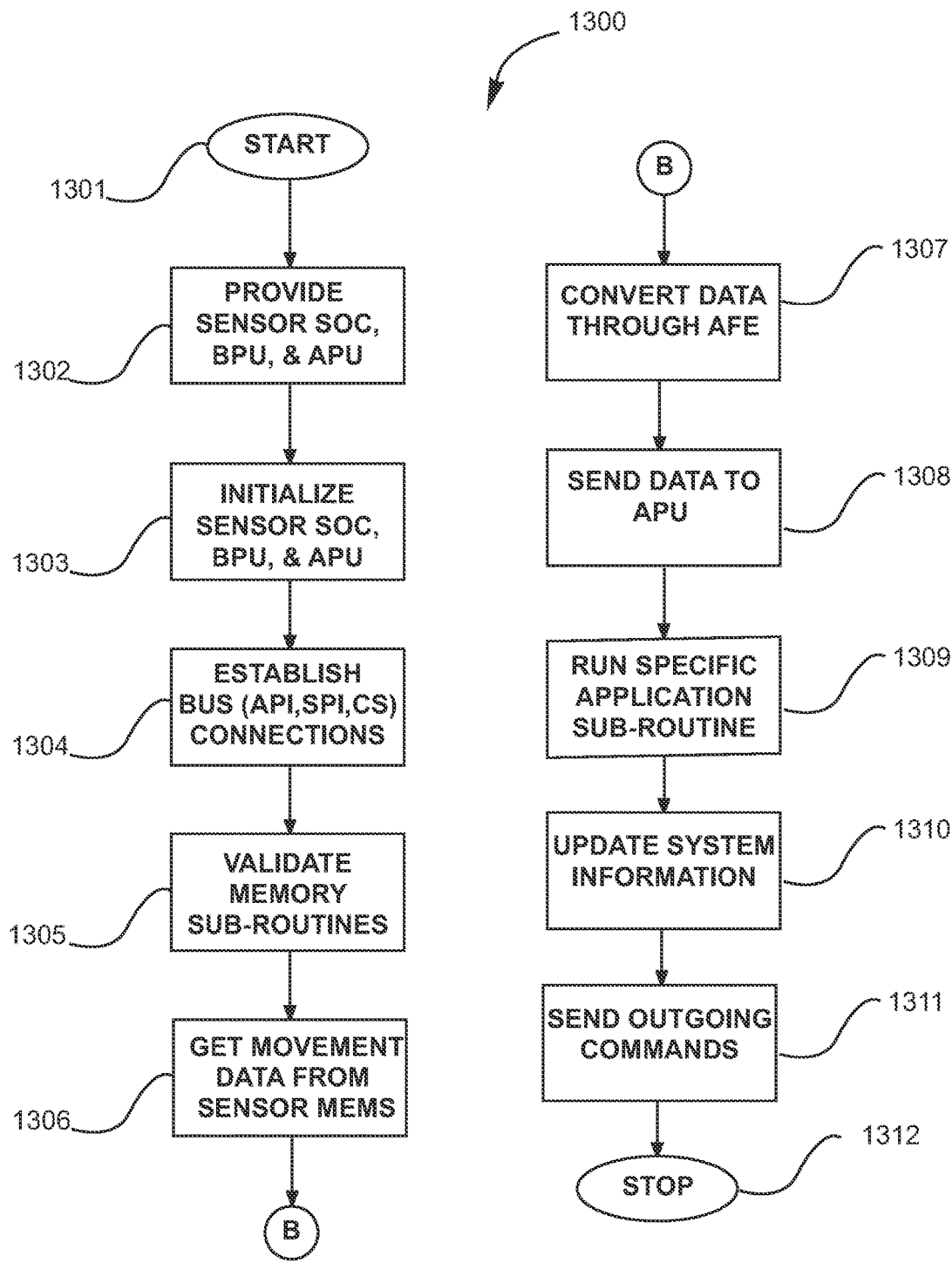
FIG. 13A-13C are simplified flow diagrams of a system-on-chip method according to yet another embodiment of the present invention.
Figure 13B:
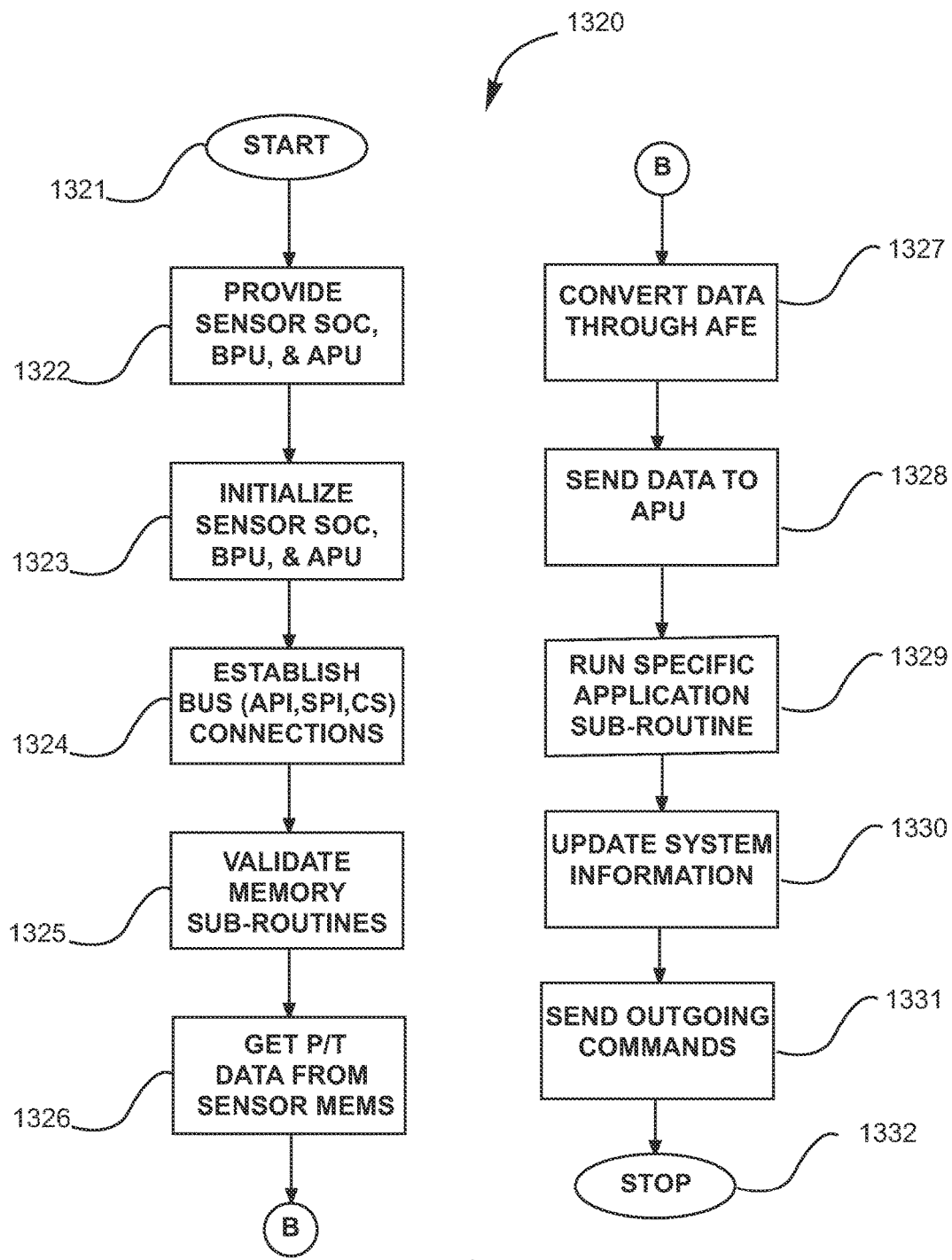
Figure 13C:
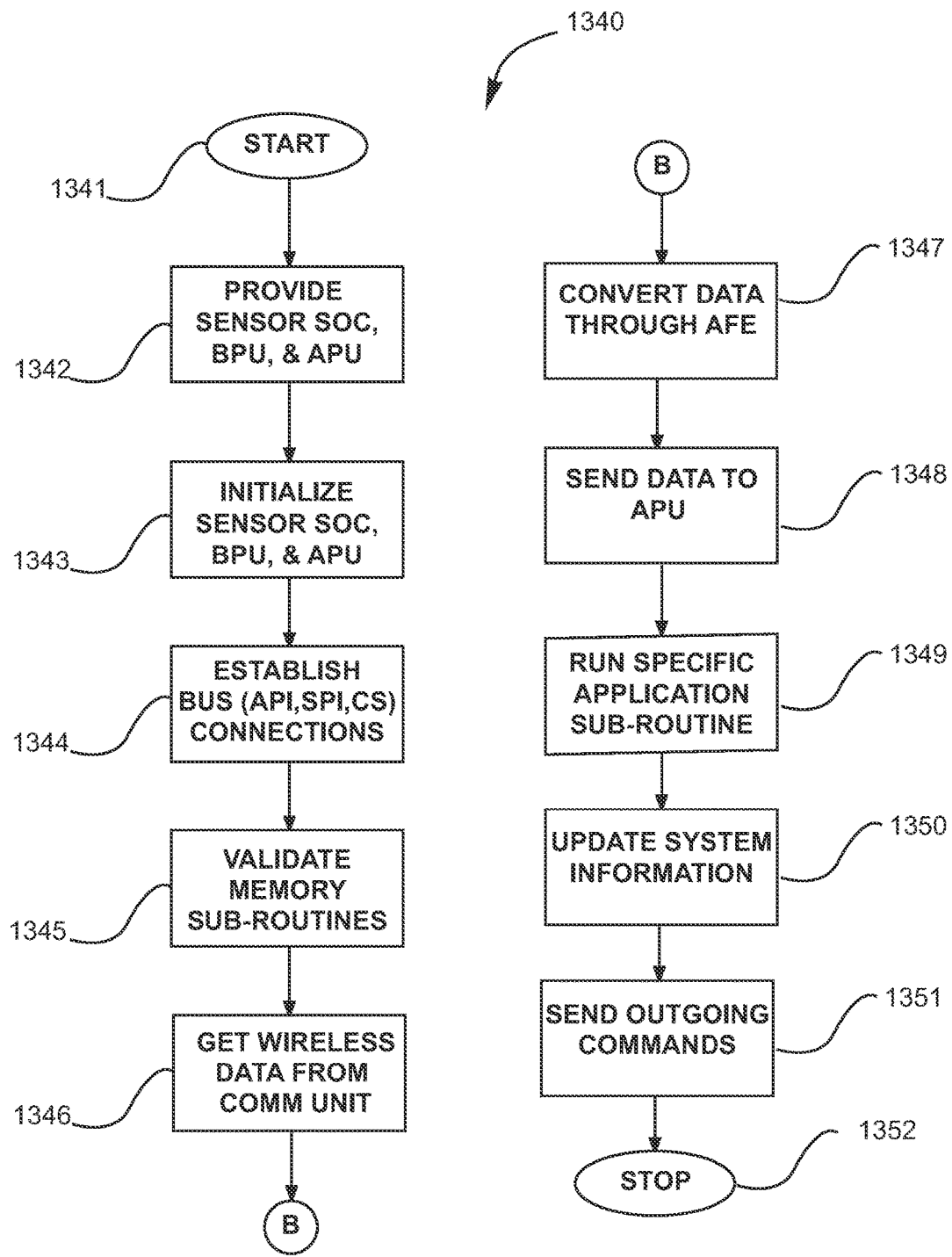

FIGS. 13A-13C are simplified flow diagrams of a system-on-chip method according to an embodiment of the present invention. These diagrams are merely examples, which should not unduly limit the scope of the claims herein. One of ordinary skill in the art would recognize other variations, modifications, and alternatives. It is also understood that the examples and embodiments described herein are for illustrative purposes only and that various modifications or changes in light thereof will be suggested to persons skilled in the art and are to be included within the spirit and purview of this process and scope of the appended claims.

As shown in FIG. 13A, the present method can be briefly outline below.
1. Start;
2. Provide an integrated system with an application processor, a broadband processor, and a sensor processor coupled to an analog front end (AFE) device;
3. Initialize the sensor, broadband, and application processors;
4. Establish bus connections between the sensor, broadband, and application processors;
5. Validate memory subroutines in each processor system's memory subsystem;
6. Get movement data from MEMS devices coupled to the sensor processor;
7. Convert the movement data through the AFE device;
8. Send converted movement data to the application processor via buses;
9. Run specific application subroutines required to process the movement data;
10. Update system information with the processed movement data;
11. Send outgoing commands according to the updated system state and the processed movement data; and
12. Stop.

These steps are merely examples and should not unduly limit the scope of the claims herein. As shown, the above method provides a way of operating an integrated SOC implementing a sensor processor coupled to one or more MEMS devices. In some embodiments, the method first initializes the sensor, application, and broadband processors. Following initialization, the system establishes bus connections between each processor unit and validates the application specific subroutines stored in each processor's array of memory. Once the system is ready, movement data is retrieved from the MEMS devices coupled to the sensor processor and is converted through the AFE device while being sent to the application processor. The converted data is processed via application-specific subroutines and is used to update system information and provide the basis for sending outgoing commands or messages. One of ordinary skill in the art would recognize many other variations, modifications, and alternatives. For example, various steps outlined above may be added, removed, modified, rearranged, repeated, and/or overlapped, as contemplated within the scope of the invention.

As shown in FIG. 13A, the method 1300 begins at start, step 1301. The present method provides a method and device for operating an integrated system-on-chip (SOC) according to an embodiment of the present invention. Providing versatile and accurate data processing is essential to a multi-function SOC implementation. With the integration of sensor, broadband, and application processors, the integrated SOC has the potential to become key micro controller system for virtually all electronic applications known today. Here, the method begins at an integrated processor system implemented on a general purpose platform.

The integrated system including a sensor processor, a broadband processor, and an application processor coupled to an analog front end (AFE) device can be used to run the multi-purpose SOC implementation, step 1302. In a specific embodiment, each processor can include a single processor, multiple processors, or a number of local or distributed processors operating in parallel. The SOC is integrated with the one or more application processors, which can be coupled to both one or more sensor processors and one or more baseband processors. Additionally, the one or more sensor processors are coupled to at least two or more MEMS devices and one or more AFE devices in this specific embodiment. One skilled in the art would recognize many variations, modifications, and alternatives.

The integrated SOC begins the system initialization by first initializing each of the associated processors and its subsystems, step 1303. In some embodiments, the each processor system has a processor device such as a micro processor unit (MPU), micro controller unit (MCU), or other programmable controller. Additionally, each processor system includes an array of programmable memory and interfaces modules such as buses. The sensor processor system also comprises as least two or more MEMS devices, while both the sensor and broadband processor systems include one or more AFE devices. Again, one skilled in the art would recognize the vast number of variations, modifications, as well as alternatives.

Following the initialization of each processor, the bus connections between each of the processors are established, step 1304. To communicate between the many subsystems, various bus interfaces can be used. In one embodiment, the one or more sensor processors are coupled to the one or more baseband processors using both a serial peripheral interface (SPI) bus and a CS interface. Additionally, the one or more application processors are coupled to the one or more sensor processors using both an application programming interface (API) bus and a SPI bus. In other embodiments, different bus types can be used to replace or augment the function of the serial peripheral, application programming, and CS interfaces. Those with ordinary skill in the art will recognize the many possibilities of modifying or using different subsystems to transfer data between processing components, and electrical buses to transfer electrical signals.

Once the bus connections are established, each processor's memory subroutines are validated to ensure proper functioning and processing of data, step 1305. In some embodiments, the sensor processor unit is configured to output one of a plurality of logic modes, which are respectively associated with a plurality of extrinsic properties, e.g., free fall, tap, specific-axis acceleration, specific-axis deceleration, and rotation. In a specific embodiment, the plurality of logic modes is respectively associated with a plurality of extrinsic properties such that each of the extrinsic properties defines a movement state of an application. These logic modes can be stored in the processor's memory subsystem. Additionally, the broadband processor unit can be configured to output one of a plurality of logic modes that are associated with different communication properties, while the application processor unit can be configured to output one or a plurality of logic modes that are associated with different information processing properties. These configurations can be varied, modified, or replaced to produce reliable operation and communication within and through the integrated SOC.

Having initialized all subsystems and established all connections or selected one or more of the subsystems and connections, the SOC is ready to receive movement data from the MEMS devices that are coupled to the sensor processor, step 1306. The movement data can include changes in system state related to body rotation, tap functions, free fall, and specific-axis acceleration/deceleration. The movement data is converted through an AFE device in order to be useable with the other processor systems, step 1307. The AFE device can include modules such as an analog to digital (ADC) converter device, as well as many others. The converted data is then sent through the bus connections, step 1308, to the application processor where specific application subroutines are run to process the converted movement data, step 1309. These specific application subroutines can include a plurality of computational algorithms used to produce other related data, or they can be related to logic mode functions that determine new system states and associated commands that should be sent. Using the processed movement data and computed data, the system can be updated to reflect the new information, step 1310. From the computed data, further outgoing commands can be sent according to the updated system state and the processed movement data, step 1311. Following this step, the system can be ready to receive additional movement data for further processing. It should be known that those skilled in the art would recognize many variations, modifications, and alternatives.

The above sequence of steps provides a method of operating an integrated SOC according to an embodiment of the present invention. The SOC includes at least a broadband processor, an application processor, and a sensor processor coupled to at least two or more MEMS devices and one or more AFE devices. Other alternatives can also be provided where steps are added, one or more steps are removed, or one or more steps are provided in a different sequence without departing from the scope of the claims herein. Further details of the present method can be found throughout the present specification.

As shown in FIG. 13B, the present method can be briefly outline below.
1. Start;
2. Provide an integrated system with an application processor, a broadband processor, and a sensor processor coupled to an analog front end (AFE) device;
3. Initialize the sensor, broadband, and application processors;
4. Establish bus connections between the sensor, broadband, and application processors;
5. Validate memory subroutines in each processor system's memory subsystem;
6. Get pressure/temperature data from MEMS devices coupled to the sensor processor;
7. Convert the pressure/temperature data through the AFE device;
8. Send converted pressure/temperature data to the application processor via buses;
9. Run specific application subroutines required to process the pressure and temperature data;
10. Update system information with the processed temperature/pressure data;
11. Send outgoing commands according to the updated system state and the processed pressure/temperature data; and
12. Stop.

These steps are merely examples and should not unduly limit the scope of the claims herein. As shown, the above method provides a way of operating an integrated SOC implementing a sensor processor coupled to one or more MEMS devices. In some embodiments, the method first initializes the sensor, application, and broadband processors. Following initialization, the system establishes bus connections between each processor unit and validates the application specific subroutines stored in each processor's array of memory. Once the system is ready, pressure and temperature data is retrieved from the MEMS devices coupled to the sensor processor and is converted through the AFE device while being sent to the application processor. The converted data is processed via application-specific subroutines and is used to update system information and provide the basis for sending outgoing commands or messages. One of ordinary skill in the art would recognize many other variations, modifications, and alternatives. For example, various steps outlined above may be added, removed, modified, rearranged, repeated, and/or overlapped, as contemplated within the scope of the invention.

As shown in FIG. 13B, the method 1320 begins at start, step 1321. The present method provides a method and device for operating an integrated system-on-chip (SOC) according to an embodiment of the present invention. Providing versatile and accurate data processing is essential to a multi-function SOC implementation. With the integration of sensor, broadband, and application processors, the integrated SOC has the potential to become key micro controller system for virtually all electronic applications known today. Here, the method begins at an integrated processor system implemented on a general purpose platform.

The integrated system including a sensor processor, a broadband processor, and an application processor coupled to an analog front end (AFE) device can be used to run the multi-purpose SOC implementation, step 1322. In a specific embodiment, each processor can include a single processor, multiple processors, or a number of local or distributed processors operating in parallel. The SOC is integrated with the one or more application processors, which can be coupled to both one or more sensor processors and one or more baseband processors. Additionally, the one or more sensor processors are coupled to at least two or more MEMS devices and one or more AFE devices in this specific embodiment. One skilled in the art would recognize many variations, modifications, and alternatives.

The integrated SOC begins the system initialization by first initializing each of the associated processors and its subsystems, step 1323. In some embodiments, the each processor system has a processor device such as a micro processor unit (MPU), micro controller unit (MCU), or other programmable controller. Additionally, each processor system includes an array of programmable memory and interfaces modules such as buses. The sensor processor system also comprises as least two or more MEMS devices, while both the sensor and broadband processor systems include one or more AFE devices. Again, one skilled in the art would recognize the vast number of variations, modifications, as well as alternatives.

Following the initialization of each processor, the bus connections between each of the processors are established, step 1324. To communicate between the many subsystems, various bus interfaces can be used. In one embodiment, the one or more sensor processors are coupled to the one or more baseband processors using both a serial peripheral interface (SPI) bus and a CS interface. Additionally, the one or more application processors are coupled to the one or more sensor processors using both an application programming interface (API) bus and a SPI bus. In other embodiments, different bus types can be used to replace or augment the function of the serial peripheral, application programming, and CS interfaces. Those with ordinary skill in the art will recognize the many possibilities of modifying or using different subsystems to transfer data between processing components, and electrical buses to transfer electrical signals.

Once the bus connections are established, each processor's memory subroutines are validated to ensure proper functioning and processing of data, step 1325. In some embodiments, the sensor processor unit is configured to output one of a plurality of logic modes, which are respectively associated with a plurality of extrinsic properties, e.g., temperature increase/decrease, pressure increase/decrease, and reaching target temperature/pressure values. In a specific embodiment, the plurality of logic modes is respectively associated with a plurality of extrinsic properties such that each of the extrinsic properties defines a pressure and temperature state of an application. These logic modes can be stored in the processor's memory subsystem. Additionally, the broadband processor unit can be configured to output one of a plurality of logic modes that are associated with different communication properties, while the application processor unit can be configured to output one or a plurality of logic modes that are associated with different information processing properties. These configurations can be varied, modified, or replaced to produce reliable operation and communication within and through the integrated SOC.

Having initialized all subsystems and established all connections or selected one or more of the subsystems and connections, the SOC is ready to receive pressure and temperature data from the MEMS devices that are coupled to the sensor processor, step 1326. The pressure and temperature data can include changes in system state related to temperature increase/decrease, pressure increase/decrease, and reaching target temperature/pressure values. The pressure and temperature data is converted through an AFE device in order to be useable with the other processor systems, step 1327. The AFE device can include modules such as an analog to digital (ADC) converter device, as well as many others. The converted data is then sent through the bus connections, step 1328, to the application processor where specific application subroutines are run to process the converted pressure and temperature data, step 1329. These specific application subroutines can include a plurality of computational algorithms used to produce other related data, or they can be related to logic mode functions that determine new system states and associated commands that should be sent. Using the processed pressure and temperature data and computed data, the system can be updated to reflect the new information, step 1330. From the computed data, further outgoing commands can be sent according to the updated system state and the processed pressure and temperature data, step 1331. Following this step, the system can be ready to receive additional pressure and temperature data for further processing. It should be known that those skilled in the art would recognize many variations, modifications, and alternatives.

The above sequence of steps provides a method of operating an integrated SOC according to an embodiment of the present invention. The SOC includes at least a broadband processor, an application processor, and a sensor processor coupled to at least two or more MEMS devices and one or more AFE devices. Other alternatives can also be provided where steps are added, one or more steps are removed, or one or more steps are provided in a different sequence without departing from the scope of the claims herein. Further details of the present method can be found throughout the present specification.

As shown in FIG. 13C, the present method can be briefly outline below.

1. Start;
2. Provide an integrated system with an application processor, a broadband processor, and a sensor processor coupled to an analog front end (AFE) device;
3. Initialize the sensor, broadband, and application processors;
4. Establish bus connections between the sensor, broadband, and application processors;
5. Validate memory subroutines in each processor system's memory subsystem;
6. Get wireless data from wireless devices coupled to the broadband processor;
7. Convert the wireless data through the AFE device;
8. Send converted wireless data to the application processor via buses;
9. Run specific application subroutines required to process the wireless data;
10. Update system information with the processed wireless data;
11. Send outgoing commands according to the updated system state and the processed wireless data; and
12. Stop.

These steps are merely examples and should not unduly limit the scope of the claims herein. As shown, the above method provides a way of operating an integrated SOC implementing a sensor processor coupled to one or more MEMS devices. In some embodiments, the method first initializes the sensor, application, and broadband processors. Following initialization, the system establishes bus connections between each processor unit and validates the application specific subroutines stored in each processor's array of memory. Once the system is ready, wireless data is retrieved from wireless devices that are coupled to the broadband processor and is converted through the AFE device while being sent to the application processor. The converted data is processed via application-specific subroutines and is used to update system information and provide the basis for sending outgoing commands or messages. One of ordinary skill in the art would recognize many other variations, modifications, and alternatives. For example, various steps outlined above may be added, removed, modified, rearranged, repeated, and/or overlapped, as contemplated within the scope of the invention.

As shown in FIG. 13C, the method 1340 begins at start, step 1341. The present method provides a method and device for operating an integrated system-on-chip (SOC) according to an embodiment of the present invention. Providing versatile and accurate data processing is essential to a multi-function SOC implementation. With the integration of sensor, broadband, and application processors, the integrated SOC has the potential to become key micro controller system for virtually all electronic applications known today. Here, the method begins at an integrated processor system implemented on a general purpose platform.

The integrated system including a sensor processor, a broadband processor, and an application processor coupled to an analog front end (AFE) device can be used to run the multi-purpose SOC implementation, step 1342. In a specific embodiment, each processor can include a single processor, multiple processors, or a number of local or distributed processors operating in parallel. The SOC is integrated with the one or more application processors, which can be coupled to both one or more sensor processors and one or more baseband processors. Additionally, the one or more sensor processors are coupled to at least two or more MEMS devices and one or more AFE devices in this specific embodiment. One skilled in the art would recognize many variations, modifications, and alternatives.

The integrated SOC begins the system initialization by first initializing each of the associated processors and its subsystems, step 1343. In some embodiments, the each processor system has a processor device such as a micro processor unit (MPU), micro controller unit (MCU), or other programmable controller. Additionally, each processor system includes an array of programmable memory and interfaces modules such as buses. The sensor processor system also comprises as least two or more MEMS devices, while both the sensor and broadband processor systems include one or more AFE devices. Again, one skilled in the art would recognize the vast number of variations, modifications, as well as alternatives.

Following the initialization of each processor, the bus connections between each of the processors are established, step 1344. To communicate between the many subsystems, various bus interfaces can be used. In one embodiment, the one or more sensor processors are coupled to the one or more baseband processors using both a serial peripheral interface (SPI) bus and a CS interface. Additionally, the one or more application processors are coupled to the one or more sensor processors using both an application programming interface (API) bus and a SPI bus. In other embodiments, different bus types can be used to replace or augment the function of the serial peripheral, application programming, and CS interfaces. Those with ordinary skill in the art will recognize the many possibilities of modifying or using different subsystems to transfer data between processing components, and electrical buses to transfer electrical signals.

Once the bus connections are established, each processor's memory subroutines are validated to ensure proper functioning and processing of data, step 1345. In some embodiments, the sensor processor unit is configured to output one of a plurality of logic modes, which are respectively associated with a plurality of extrinsic properties, e.g., free fall, tap, specific-axis acceleration, specific-axis deceleration, and rotation. In a specific embodiment, the plurality of logic modes is respectively associated with a plurality of extrinsic properties such that each of the extrinsic properties defines a movement state of an application. These logic modes can be stored in the processor's memory subsystem. Additionally, the broadband processor unit can be configured to output one of a plurality of logic modes that are associated with different communication properties, while the application processor unit can be configured to output one or a plurality of logic modes that are associated with different information processing properties. These configurations can be varied, modified, or replaced to produce reliable operation and communication within and through the integrated SOC.

Having initialized all or some of subsystems and established all or some of the connections, the SOC is ready to receive wireless data from wireless devices that are coupled to the broadband processor, step 1346. The wireless data can include data formatted according to a variety of wireless communication protocols, such as GPS, FM, Bluetooth, or Zigbee/Zwave. The wireless data is converted through an AFE device in order to be useable with the other processor systems, step 1347. The AFE device can include modules such as an analog to digital (ADC) converter device, as well as many others. The converted data is then sent through the bus connections, step 1348, to the application processor where specific application subroutines are run to process the converted wireless data, step 1349. These specific application subroutines can include a plurality of computational algorithms used to produce other related data, or they can be related to logic mode functions that determine new system states and associated commands that should be sent. Using the processed wireless data and computed data, the system can be updated to reflect the new information, step 1350. From the computed data, further outgoing commands can be sent according to the updated system state and the processed wireless data, step 1351. Following this step, the system can be ready to receive additional wireless data for further processing. It should be known that those skilled in the art would recognize many variations, modifications, and alternatives.

The above sequence of steps provides a method of operating an integrated SOC according to an embodiment of the present invention. The SOC includes at least a broadband processor, an application processor, and a sensor processor coupled to at least two or more MEMS devices and one or more AFE devices. Other alternatives can also be provided where steps are added, one or more steps are removed, or one or more steps are provided in a different sequence without departing from the scope of the claims herein. Further details of the present method can be found throughout the present specification.

FIG. 14 is a simplified top diagram of a component of an integrated MEMS-CMOS system according to an embodiment of the present invention. More particularly, the component can be a transducer apparatus, which can be a component of an inertial sensing device, such as an accelerometer. As shown, apparatus 1400 includes a movable base structure 1410, at least one intermediate anchor structure 1420, and at least one intermediate spring structure 1430. In an embodiment, apparatus 1400 can be configured to improve tolerance of external deformations. Those of ordinary skill in the art will recognize other variations, modifications, and alternatives.

In various embodiments, movable base structure 1410 can have an outer surface region, and have at least one portion removed to form at least one inner surface region 1402. In a specific embodiment, movable base structure 1410 can be formed from a single crystal silicon, polycrystalline silicon, or amorphous silicon material. Moveable base structure 1410 can also include a thickness of a polymer or a thickness of a metal material. In other embodiments, movable base structure 1410 can include other materials and combinations thereof. In a specific embodiment, movable base structure 1410 can be a rectangular movable base structure, a patterned polygonal base structure, or the like. Those skilled in the art will recognize other variations, modifications, and alternatives.

In various embodiments, intermediate anchor structure(s) 1420 can be spatially disposed within a vicinity of inner surface region(s) 1402 of the movable base structure. In a specific embodiment, intermediate anchor structure(s) 1420 can be formed from single crystal silicon, polycrystalline silicon, amorphous silicon material, or the like. Intermediate anchor structure(s) 1420 can also include a polymer or metal material, or other materials or combinations thereof. Of course, there can be other variations, modifications, and alternatives.

In an embodiment, intermediate spring structure(s) 1430 can be operably coupled to the intermediate anchor structure(s) 1420 and at least one portion of inner surface region(s) 1402 of movable base structure 1410. In a specific embodiment, intermediate spring structure(s) 1430 can be formed from single crystal silicon, polycrystalline silicon, amorphous silicon material, or the like. Intermediate spring structure(s) 1430 can also include a polymer or metal material, or other materials or combinations thereof. In a specific embodiment, intermediate spring structure(s) 1430 can be spatially oriented to be substantially 45 degrees or substantially (pi/4) radians to the edges of the die. The intermediate spring structure(s) can have at least one segment having a segment length. To determine the orientation of a spring, the segments of the spring, which are connected by folds, are used as a reference. The segments would be positioned such that the segments are perpendicular to diagonal lines 1401. Another way to determine the orientation of a spring can be done by drawing a "line" connecting the contacts of the spring from the anchor to the movable base (i.e. the end points of the spring). In this case, the proper orientation of the spring would have the "line" forming a substantially 45 degree or (pi/4) radian angle with the edges of a die (pointed along diagonal lines 1401). Those skilled in the art will recognize other variations, modifications, and alternatives.

In an embodiment, apparatus 1400 can include at least one capacitor element 1450 spatially disposed within a vicinity of inner surface region(s) 1402 of movable base structure 1410. As described above, intermediate anchor structure(s) 1420 can be spatially disposed within a vicinity of inner surface region(s) 1402 of the movable base structure. The capacitor element(s) can include a fixed capacitor element and a movable capacitor element. The movable capacitor element will generally be disposed in a portion of the movable base structure 1410. The fixed capacitor element can be part of the intermediate anchor structure 1420. In a specific embodiment, the physical basis of apparatus 1400 is to have the average displacement of the fixed capacitor element(s) match the average displacement of the movable capacitor element(s) in response to external deformations. Of course, there can be other variations, modifications, and alternatives.

In an embodiment, apparatus 1400 can be coupled to another MEMS device or an electronic device. In a specific embodiment, apparatus 1400 can be configured to be tolerant of external deformations. Apparatus 1400 can be a transducer apparatus which reduces the area needed for anchors and springs and provides more area for other MEMS components. There can be other variations, modifications, and alternatives as well. Further embodiments of the above device may be found in the co-pending patent application, referred to above.

FIG. 15 is a simplified top diagram of a component of an integrated MEMS-CMOS system according to various embodiments of the present invention. More particularly, the component can be an inertial sensing device, such as a gyroscope. As shown, device 1500, which can be disposed upon a substrate having a surface region, includes at least one anchor structure 1510, at least one frame structure 1520, at least one movable structure, at least one first flexible member, and at least one second flexible member. In an embodiment, the movable structure(s) can include at least one peripheral movable structure 1530 and at least one central movable structure 1540. The first flexible member(s) can include flexible anchor member(s) 1550 and the second flexible member(s) can include at least one flexible frame member 1560 and/or at least one flexible structure member 1570. Those of ordinary skill in the art will recognize other variations, modifications, and alternatives.

In a specific embodiment, the substrate can include a buried oxide (BOX) substrate. The substrate can include an epitaxial (EPI) material. In further embodiments, the substrate can have a silicon, single crystal silicon, or polycrystalline silicon material. The substrate can also include a dielectric material, a metal material, a metal alloy, or other materials or combination of materials thereof. In a specific embodiment, the substrate can have an integrated circuit layer, such as a CMOS device layer, formed overlying the substrate. Those skilled in the art will recognize other variations, modifications, and alternatives.

In various embodiments, the substrate includes a surface region. At least one anchor structure 1510 can be formed overlying the surface region. At least one flexible anchor member 1550 is coupled to at least a portion of the anchor structure(s). In various embodiments, anchor structure(s) 1510 and flexible anchor member(s) 1550 can include a silicon, dielectric, metal, alloy, or other materials or combination thereof. In a specific embodiment, flexible anchor members 1550 can include torsion spring(s) or bending spring(s). In further embodiments, anchor structure(s) 1510 and flexible anchor member(s) 1550 can be formed together during the same fabrication processes or separately by performing a wet or dry etching or mechanical process. Of course, there can be other variations, modifications, and alternatives.

In an embodiment, frame structure(s) 1520 can be formed having at least a portion coupled to flexible anchor member(s) 1550. Flexible frame member(s) 1560 can be formed and coupled to at least a portion of frame structure(s) 1520. In embodiments wherein more than one frame structure 1520 is formed, at least one flexible coupling member 1580 can be formed to couple frame structure(s) 1520. In various embodiments, frame structure(s) 1520, flexible coupling member(s) 1580 and flexible frame member(s) 1560 can include a silicon, dielectric, metal, alloy, or other materials or combinations thereof. In a specific embodiment, flexible frame member(s) 1560 and flexible coupling member(s) 1580 can include torsion spring(s) or bending spring(s). In further embodiments, frame structure(s) 1520, flexible coupling member(s) 1580, and flexible frame member(s) 1560 can be formed together during the same fabrication processes or separately by performing a wet or dry etching or mechanical process. As stated previously, there can be other variations, modifications, and alternatives.

In various embodiments, peripheral movable structure(s) 1530 can be formed overlying the substrate, having at least one portion coupled to flexible frame member(s) 1560. The movable structure(s), which can be peripheral movable structure(s) 1530, can have at least one flexible tilting member. Flexible structure member(s) 1570 can be formed and coupled to at least a portion of peripheral movable structure(s) 1530. Also, flexible structure member(s) 1570 can be coupled to central movable structure(s) 1540, which can be formed overlying the substrate. In various embodiments, peripheral movable structure 1530, central movable structure 1540, flexible structure and tilting member(s) (referring to flexible structure member(s) 1570) can include a silicon, dielectric, metal, alloy, or other materials or combinations thereof. In a specific embodiment, the flexible structure and tilting member(s) (referring to flexible structure member(s) 1570) can include torsion spring(s) or bending spring(s). Other torsion springs or bending springs can also be formed within at least one portion of central movable structure(s) 1540, such as the underside of central movable structure(s) 1540 which overlies the substrate.

The movable structures can be formed within frame structure(s) 1520. In the example illustrated in FIG. 15, four peripheral movable structures 1530 and two central movable structures 1540 are shown formed within two frame structures 1520. Each frame structures 1520 are coupled to two peripheral movable structures 1530 and one central movable structure 1540. The peripheral and central movable structures 1530/1540 can be proof masses, which can be predetermined test masses used in a measuring device. In further embodiments, the peripheral and central movable structure(s) 1530/1540 and the flexible structure and tilting member(s) [referring to flexible structure member(s) 1570] can be formed together or separately by performing a wet or dry etching or mechanical process. Again, there can be other variations, modifications, and alternatives.

At least one comb structure 1590 can be formed and coupled to at least one portion of frame structure(s) 1520. In various embodiments, comb structure(s) 1590 can be anti-phase driving comb structure(s), which can include a silicon, dielectric, metal, alloy, or other materials or combinations thereof. Additionally, the peripheral and central movable structure(s) 1530/1540 can have stop structures 1501, which can be used to set the boundaries of any vibration, movement, or displacement. A portion of peripheral movable structure 1530 and central movable structure 1540 may be removed. In specific embodiments, peripheral movable structure 1530 and central movable structure 1540 perforations within a line or an array of perforations. In some embodiments, the perforations can be formed by performing an etching process or mechanical process. In various embodiments, all elements mentioned previous can be formed by performing an etching process on one wafer or material. Of course, there can be other variations, modifications, and alternatives. Further embodiments of the above device are disclosed in the co-pending patent application referred to above.

FIG. 16 is a simplified top diagram of a component of an integrated MEMS-CMOS system according to an embodiment of the present invention. This diagram, which can represent a partially formed three-axis magnetic field sensor device or a two-axis magnetic field sensor device, is merely an example, which should not unduly limit the scope of the claims herein. One of ordinary skill in the art would recognize many other variations, modifications, and alternatives. As shown, device 1600 includes a substrate 1610, an integrated circuit (IC) layer 1620, a first magnetic field sensor element 1630, and a second magnetic field sensor element 1640. Those skilled in the art will recognize other variations, modifications, and alternatives.

In an embodiment, substrate 1610 can have a surface region. In a specific embodiment, substrate 1610 can include a buried oxide (BOX) substrate. Substrate 1610 can include a substrate-on-insulator (SOI) substrate. In another specific embodiment, substrate 1610 can include an epitaxial (EPI) material. In further embodiments, substrate 1610 can have a silicon, single crystal silicon, or polycrystalline silicon material. Substrate 1610 can also include metals, dielectrics, polymers, and other materials and combinations thereof. Those skilled in the art will recognize other variations, modifications, and alternatives.

In an embodiment, IC layer 1620 can be formed overlying at least one portion of the surface region. In a specific embodiment, IC layer 1620 can include an application specific integrated circuit (ASIC) layer, or other type of IC layer or combination thereof. Also, IC layer 1620 can include at least one IC device, CMOS device, or other device. IC layer 1620 can be coupled to the first and second magnetic field sensor elements 1630 and 1640. Those skilled in the art will recognize other variations, modifications, and alternatives.

In an embodiment, first magnetic field sensor element(s) 1630 and second magnetic field sensor element 1640 can be formed overlying at least one portion of the surface region. Magnetic field sensor elements 1630 and 1640 can include ordinary magneto-resistive (OMR) device(s), anisotropic magneto-resistive (AMR) device(s), giant magneto-resistive (GMR) device(s), or tunnel junction magneto-resistive (TMR) device(s). Elements 1630 and 1640 can also be other types of magnetic field sensor devices, sensors, or combinations thereof. In a specific embodiment, magnetic field sensor elements 1630 and 1640 can include thin film devices that can be deposited overlying at least one portion of the surface region. The thin film device(s) can be deposited by a sputtering process or an electric plating process. In a specific embodiment, magnetic field sensor elements 1630 and 1640 are formed as a Wheatstone bridge, a half bridge, or a single element configuration. In an embodiment, magnetic field sensor elements 1630 and 1640 can include at least one layer of dielectric material and/or metal material. As stated previously, there can be other variations, modifications, and alternatives. Further embodiments of the above device are disclosed in the co-pending patent application referred to above.

Figure 17:
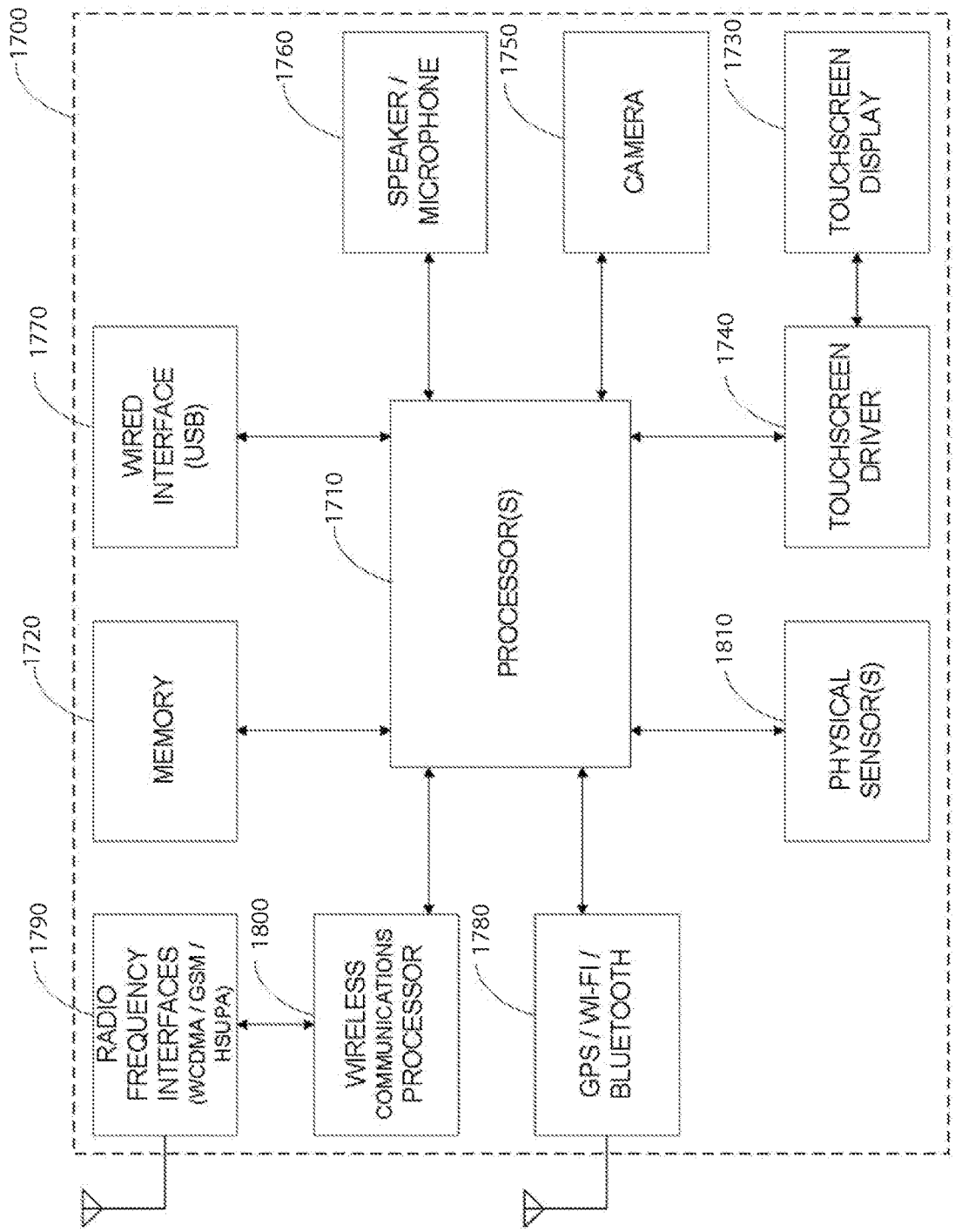
FIG. 17 is a simplified block diagram of a device incorporating various embodiments of the present invention.

FIG. 17 illustrates a functional block diagram of various embodiments of the present invention. In FIG. 17, a computing device or computing system 1700 typically includes an applications processor 1710, memory 1720, a touch screen display 1730 and driver 1740, an image acquisition device 1750, audio input/output devices 1760, and the like. Additional communications from and to computing device are typically provided by via a wired interface 1770, a GPS/Wi-Fi/Bluetooth interface 1780, RF interfaces 1790 and driver 1800, and the like. Also included in various embodiments are physical sensors 1810.

In various embodiments, computing device 1700 may be a hand-held computing device (e.g. Apple iPad, Apple iTouch, Dell Mini slate/Streak, Lenovo Skylight/IdeaPad, Samsung Galaxy Tab, Asus EEE series, HP Slate, Notion Ink Adam), a portable telephone (e.g. Apple iPhone, Motorola Droid, Google Nexus One, HTC Incredible/EVO 4G, Palm Pre series, Nokia N900), a portable computer (e.g. netbook, laptop), a media player (e.g. Microsoft Zune, Apple iPod), a reading device (e.g. Amazon Kindle, Barnes and Noble Nook), or the like.

Typically, computing device 1700 may include one or more processors 1710. Such processors 1710 may also be termed application processors, and may include a processor core, a video/graphics core, and other cores. Processors 1710 may be a processor from Apple (A4), Intel (Atom), NVidia (Tegra 2), Marvell (Armada), Qualcomm (Snapdragon), Samsung, TI (OMAP), or the like. In various embodiments, the processor core may be an Intel processor, an ARM Holdings processor such as the Cortex-A, -M, -R or ARM series processors, or the like. Further, in various embodiments, the video/graphics core may be an Imagination Technologies processor PowerVR-SGX, -MBX, -VGX graphics, an Nvidia graphics processor (e.g. GeForce), or the like. Other processing capability may include audio processors, interface controllers, and the like. It is contemplated that other existing and/or later-developed processors may be used in various embodiments of the present invention.

In various embodiments, memory 1720 may include different types of memory (including memory controllers), such as flash memory (e.g. NOR, NAND), pseudo SRAM, DDR SDRAM, or the like. Memory 1720 may be fixed within computing device 1700 or removable (e.g. SD, SDHC, MIVIC, MINI SD, MICRO SD, CF, SIM). The above are examples of computer readable tangible media that may be used to store embodiments of the present invention, such as computer-executable software code (e.g. firmware, application programs), application data, operating system data or the like. It is contemplated that other existing and/or later-developed memory and memory technology may be used in various embodiments of the present invention.

In various embodiments, touch screen display 1730 and driver 1740 may be based upon a variety of later-developed or current touch screen technology including resistive displays, capacitive displays, optical sensor displays, electromagnetic resonance, or the like. Additionally, touch screen display 1730 may include single touch or multiple-touch sensing capability. Any later-developed or conventional output display technology may be used for the output display, such as TFT-LCD, OLED, Plasma, trans-reflective (Pixel Qi), electronic ink (e.g. electrophoretic, electrowetting, interferometric modulating). In various embodiments, the resolution of such displays and the resolution of such touch sensors may be set based upon engineering or non-engineering factors (e.g. sales, marketing). In some embodiments of the present invention, a display output port, such as an HDMI-based port or DVI-based port may also be included.

In some embodiments of the present invention, image capture device 1750 may include a sensor, driver, lens and the like. The sensor may be based upon any later-developed or convention sensor technology, such as CMOS, CCD, or the like. In various embodiments of the present invention, image recognition software programs are provided to process the image data. For example, such software may provide functionality such as: facial recognition, head tracking, camera parameter control, or the like.

In various embodiments, audio input/output 1760 may include conventional microphone(s)/speakers. In some embodiments of the present invention, three-wire or four-wire audio connector ports are included to enable the user to use an external audio device such as external speakers, headphones or combination headphone/microphones. In various embodiments, voice processing and/or recognition software may be provided to applications processor 1710 to enable the user to operate computing device 1700 by stating voice commands. Additionally, a speech engine may be provided in various embodiments to enable computing device 1700 to provide audio status messages, audio response messages, or the like.

In various embodiments, wired interface 1770 may be used to provide data transfers between computing device 1700 and an external source, such as a computer, a remote server, a storage network, another computing device 1700, or the like. Such data may include application data, operating system data, firmware, or the like. Embodiments may include any later-developed or conventional physical interface/protocol, such as: USB 2.0, 3.0, micro USB, mini USB, Firewire, Apple iPod connector, Ethernet, POTS, or the like. Additionally, software that enables communications over such networks is typically provided.

In various embodiments, a wireless interface 1780 may also be provided to provide wireless data transfers between computing device 1700 and external sources, such as computers, storage networks, headphones, microphones, cameras, or the like. As illustrated in FIG. 17, wireless protocols may include Wi-Fi (e.g. IEEE 802.11 a/b/g/n, WiMax), Bluetooth, IR and the like.

GPS receiving capability may also be included in various embodiments of the present invention, however is not required. As illustrated in FIG. 17, GPS functionality is included as part of wireless interface 1780 merely for sake of convenience, although in implementation, such functionality is currently performed by circuitry that is distinct from the Wi-Fi circuitry and distinct from the Bluetooth circuitry.

Additional wireless communications may be provided via RF interfaces 1790 and drivers 1800 in various embodiments. In various embodiments, RF interfaces 1790 may support any future-developed or conventional radio frequency communications protocol, such as CDMA-based protocols (e.g. WCDMA), GSM-based protocols, HSUPA-based protocols, or the like. In the embodiments illustrated, driver 1800 is illustrated as being distinct from applications processor 1710. However, in some embodiments, these functionality are provided upon a single IC package, for example the Marvel PXA330 processor, and the like. It is contemplated that some embodiments of computing device 1700 need not include the RF functionality provided by RF interface 1790 and driver 1800.

FIG. 17 also illustrates computing device 1700 to include physical sensors 1810. In various embodiments of the present invention, physical sensors 1810 can be single axis or multi-axis Micro-Electro-Mechanical Systems (MEMS) based devices being developed by M-cube, the assignee of the present patent application. Physical sensors 1810 can include accelerometers, gyroscopes, pressure sensors, magnetic field sensors, bio sensors, and the like. In various embodiments, physical sensors 1810 may fabricated using the combined CMOS MEMS fabrication techniques described above. More specifically, one or more MEMS devices may be fabricated approximately in parallel using common masks, layers, and processes, above a substrate. In various embodiments, the substrate may be on top of a CMOS device. Both the CMOS and MEMS device may be fabricated using foundry-compatible processes. In other embodiments of the present invention, conventional physical sensors 1810 from Bosch, STMicroelectronics, Analog Devices, Kionix or the like may be used.

In various embodiments, any number of future developed or current operating systems may be supported, such as iPhone OS (e.g. iOS), WindowsMobile (e.g. 7), Google Android (e.g. 2.2), Symbian, or the like. In various embodiments of the present invention, the operating system may be a multi-threaded multi-tasking operating system. Accordingly, inputs and/or outputs from and to touch screen display 1730 and driver 1740 and inputs/or outputs to physical sensors 1810 may be processed in parallel processing threads. In other embodiments, such events or outputs may be processed serially, or the like. Inputs and outputs from other functional blocks may also be processed in parallel or serially, in other embodiments of the present invention, such as image acquisition device 1750 and physical sensors 1810.

FIG. 17 is representative of one computing device 1700 capable of embodying the present invention. It will be readily apparent to one of ordinary skill in the art that many other hardware and software configurations are suitable for use with the present invention. Embodiments of the present invention may include at least some but need not include all of the functional blocks illustrated in FIG. 17. For example, in various embodiments, computing device 1200 may lack image acquisition unit 1750, or RF interface 1790 and/or driver 1800, or GPS capability, or the like. Additional functions may also be added to various embodiments of computing device 1700, such as a physical keyboard, an additional image acquisition device, a trackball or trackpad, a joystick, or the like. Further, it should be understood that multiple functional blocks may be embodied into a single physical package or device, and various functional blocks may be divided and be performed among separate physical packages or devices.

These diagrams are merely examples, which should not unduly limit the scope of the claims herein. In light of the present invention disclosure, one of ordinary skill in the art would recognize many other variations, modifications, and alternatives. For example, various steps outlined above may be added, removed, modified, rearranged, repeated, and/or overlapped, as contemplated within the scope of the invention. It is also understood that the examples and embodiments described herein are for illustrative purposes only and that various modifications or changes in light thereof will be suggested to persons skilled in the art and are to be included within the spirit and purview of this process and scope of the appended claims.

What is claimed is:

1. A computing system for sensing physical status data using MEMS (Micro Electro-Mechanical System) devices, the system comprising:
    an executable memory configured to store a plurality of executable code;
    one or more application processors coupled to the memory, wherein the one or more application processors are configured to execute the plurality of executable code;
    one or more baseband processors coupled to the one or more application processors, wherein the one or more baseband processors are configured for at least a wireless communication protocol; and
    a MEMS system coupled to the application processor, wherein the MEMS system comprises:
        the MEMS devices configured to sense physical perturbations, wherein the MEMS devices includes at least a MEMS transducer apparatus comprising:
        a substrate member having a surface region,
        a movable base having at least one intermediate cavity disposed in an intermediate portion of the movable base structure, the at least one intermediate cavity having a cavity surface region;
        at least one intermediate anchor structure spatially disposed within the at least one intermediate cavity, the intermediate anchor structure(s) being coupled to at least one portion of the surface region;
        at least one intermediate spring structure coupled to at least one portion of the cavity surface region, the intermediate spring structure(s) being coupled to the intermediate anchor structure(s), the spring structure(s) being spatially oriented to be substantially 45 degrees or substantially (pi/4) radians to edges of a die; and
        at least one capacitor element, the capacitor element(s) being spatially disposed within a vicinity of the intermediate cavity; and
        one or more sensor processors coupled to the MEMS devices, wherein the one or more sensor processors are configured to provide physical status data to the one or more application processors in response to the physical perturbations sensed by the MEMS devices;
    wherein the one or more application processors are also configured to execute the plurality of executable code in response to the physical status data.

2. The system of claim 1 wherein the one or more baseband processors is configured for a GPS (Global Positioning System), a FM (Frequency Modulation), a Bluetooth, or a Zigbee/Zwave communication interface.

3. The system of claim 1 wherein the one or more sensor processors is coupled to the one or more baseband processors using at least an interface selected from a group consisting of: a serial peripheral interface bus, a CS (Chip Select) interface.

4. The system of claim 1 wherein the one or more application processors are coupled to the MEMS system using at least an interface selected from a group consisting of: application programming interface bus, a serial peripheral interface bus.

5. The system of claim 1 wherein the MEMS devices are selected from a group consisting of: an accelerometer, a gyroscope, magnetic sensor, a pressure sensor, a microphone, a humidity sensor, a temperature sensor, a chemical sensor, a biosensor, an inertial sensor.

6. The system of claim 1 wherein the one or more sensor processors are configured to output one of a plurality of logic modes.

7. The system of claim 1 wherein the one or more sensor processors are configured to output one of a plurality of logic modes, wherein the plurality of logic modes are respectively associated with a plurality of extrinsic properties, each of the extrinsic properties defining a movement state of at least one of the MEMS devices.

8. The system of claim 1 wherein the one or more sensor processors comprises an array of programmable memories.

9. The system of claim 1 wherein the one or more sensor processors is provided on a general purpose sensor platform.

10. The system of claim 1 further comprising one or more analog front end modules provided between the two or more MEMS devices and the one or more sensor processors.

11. The system of claim 1 wherein at least one of the MEMS devices is coupled to an analog front end, the analog front end is coupled to an analog to digital converter device, and wherein the analog to digital converter device is coupled to the one or more sensor processors.

12. The system of claim 1 wherein the one or more application processors is integrally coupled to the one or more sensor processors; and the one or more baseband processors is integrally coupled to the one or more sensor processors.

* * * * *